United States Patent
Zadok et al.

(10) Patent No.: US 9,163,958 B2
(45) Date of Patent: Oct. 20, 2015

(54) DISTRIBUTED SENSING EMPLOYING STIMULATED BRILLOUIN SCATTERING IN OPTICAL FIBERS

(75) Inventors: Avinoam Zadok, Givat Shmuel (IL); Yair Antman, Kfar Saba (IL); Luc Thevenaz, Yverdon-les-Bains (CH)

(73) Assignee: BAR ILAN UNIVERSITY, Ramat Gan (IL)

( * ) Notice: Subject to any disclaimer, the term of this patent is extended or adjusted under 35 U.S.C. 154(b) by 129 days.

(21) Appl. No.: 14/118,538

(22) PCT Filed: May 17, 2012

(86) PCT No.: PCT/IL2012/050179
§ 371 (c)(1),
(2), (4) Date: Nov. 18, 2013

(87) PCT Pub. No.: WO2012/156978
PCT Pub. Date: Nov. 22, 2012

(65) Prior Publication Data
US 2014/0083197 A1    Mar. 27, 2014

Related U.S. Application Data

(60) Provisional application No. 61/631,666, filed on Jan. 9, 2012, provisional application No. 61/457,717, filed on May 18, 2011.

(51) Int. Cl.
*G01J 1/04* (2006.01)
*G01D 5/26* (2006.01)
*H04B 10/071* (2013.01)
(Continued)

(52) U.S. Cl.
CPC ............ *G01D 5/268* (2013.01); *G01D 5/35348* (2013.01); *G01N 21/88* (2013.01); *H04B 10/071* (2013.01)

(58) Field of Classification Search
CPC .................. H01S 3/0675; H01S 3/094; G01N 2021/6439; G01N 21/88; G01D 5/268; G01D 5/35348
USPC ............. 250/227.14, 227.16, 227.19, 227.23, 250/221; 372/22, 28, 6, 21, 69, 70
See application file for complete search history.

(56) References Cited

U.S. PATENT DOCUMENTS

| 4,396,290 | A | 8/1983 | Morris |
| 7,283,216 | B1 | 10/2007 | Geng et al. |
| 7,873,273 | B2 * | 1/2011 | Koyamada ............... 398/28 |

(Continued)

OTHER PUBLICATIONS

Antman et al., (2012) Localized and stationary dynamic gratings via stimulated Brillouin scattering with phase modulated pumps. Opt Express 20(7): 7792-7806.

(Continued)

*Primary Examiner* — Que T Le
(74) *Attorney, Agent, or Firm* — Rothwell, Figg, Ernst & Manbeck, P.C.

(57) ABSTRACT

Disclosed are methods and devices for distributed sensing of a measurable parameter employing stimulated Brillouin scattering in an optical fiber. A frequency-modulated or phase-modulated light wave is transmitted into the optical fiber. A scattered light wave in the optical fiber is monitored for sensing a measurable parameter. In some embodiments, the calculating step may include calculating a distance of a sensed location along the optical fiber using the monitored time of arrival.

25 Claims, 12 Drawing Sheets

(51) Int. Cl.
*G01D 5/353* (2006.01)
*G01N 21/88* (2006.01)

(56) References Cited

U.S. PATENT DOCUMENTS

2003/0198260 A1  10/2003  Hogan et al.
2004/0208413 A1  10/2004  Scandale et al.
2009/0169208 A1   7/2009  Grigoryan et al.
2010/0165327 A1   7/2010  Hartog

OTHER PUBLICATIONS

Primerov et al., (2012) Brillouin Distributed Sensing Using Localized and Stationary Dynamic Gratings. SPIE Photonics Europe 2012, Brussels, Belgium. Proc SPIE 8439: 843908-1-843908-7.
Zadok et al., (2012) Random-access distributed fiber sensing. Laser Photonics Rev 6(5): L1-L5.
Zhang et al., (2004) Improvement of spatial resolution of Brillouin optical time domain reflectometer using spectral decomposition. Optica Applicata 34(2): 291-301.

* cited by examiner ent Application No. 61/457,717 filed May 18, 2011 and to U.S. Patent Application No. 61/631,666 filed Jan. 9, 2012, which are incorporated herein in their entireties.

DISTRIBUTED SENSING EMPLOYING STIMULATED BRILLOUIN SCATTERING IN OPTICAL FIBERS

CROSS REFERENCE TO RELATED APPLICATIONS

This application is a 35 U.SC. §371 National Phase Entry Application from PCT/IL2012/050179, filed May 17, 2012, and designating the United States, which claims priority under to U.S. Patent Application No. 61/457,717 filed May 18, 2011 and to U.S. Patent Application No. 61/631,666 filed Jan. 9, 2012, which are incorporated herein in their entireties.

TECHNICAL FIELD

The invention, in some embodiments, relates to the field of distributed sensing using an optical fiber and more particularly, but not exclusively, to methods and devices that employ stimulated Brillouin scattering in optical fibers.

BACKGROUND

Distributed sensing is commonly used to determine the conditions of a monitored object by collecting data from a distributed set of points on or in the vicinity of the object. The technique is widely used for example for structural health monitoring (SHM), where a structure such as a bridge, a building or an airplane, is monitored substantially simultaneously at the distributed set of points, to detect a structural fault at an early stage of the fault progress.

Some methods for distributed sensing utilize a deployed optical fiber, which is in mechanical or thermal contact, substantially along at least a portion of the fiber's length, with the object that needs to be monitored. Optical fibers, typically made as flexible transparent thin fibers, are commonly used for highly efficient transportation of light signals over large distances. Within some such methods for distributed sensing, each point, area, or segment of the optical fiber may be used for sensing; light signals, indicating sensed data, are transmitted through the fiber to be collected and processed at any one or both of the optical fiber's ends.

Stimulated Brillouin scattering (SBS) in optical fibers is an underlying effect employed by several methods for distributed sensing of local strain and temperature variations, over distances that may reach tens of kilometers. Techniques that employ SBS are for example Brillouin Optical Time Domain Reflectometry (BOTDR), Brillouin Optical Time Domain Analysis (BOTDA) and Brillouin Optical correlation Domain Analysis (BOCDA). Within these techniques, an intense light wave (a pump wave)—that may be amplitude-modulated, frequency-modulated or phase-modulated—is transmitted to the fiber, while a scattered light wave, generally having a frequency shifted from that of the pump wave, is received from the optical fiber, monitored and analyzed in the time and frequency domains.

Stimulated Brillouin scattering (SBS) is a nonlinear optical propagation effect, in which an optical wave (a pump wave) propagating forward in an optical medium, is scattered inelastically by phonons of the medium. The phonons are acoustic waves, generated in the medium by the propagating pump light wave, through electrostriction.

When SBS occurs in an optical fiber, the pump light wave may be backscattered by the phonons in the optical fiber that are generated as described above, thereby generating a backscattered light wave propagating in the opposite direction to the pump light wave. The frequency of the backscattered wave is different from the frequency of the pump wave by the Brillouin frequency shift $\Omega_B$, which is generally on the order of magnitude of 10 GHz in standard optical fibers. The $\Omega_B$ frequency is a property of the optical medium in which the waves propagate, but it may vary with environmental conditions such as temperature and mechanical strain. Further, when SBS is generated in an optical fiber, and a second optical wave (a probe wave) is transmitted into the fiber in the opposite direction to the pump wave, the probe wave may be forward-scattered by the phonons in the optical fiber that are generated as described above. The forward-scattered probe light wave may further be amplified considerably if its frequency is set to be substantially equal to that of the backscattered wave, namely if its frequency is shifted from that of the pump light wave by exactly $\Omega_B$.

In BOTDR, a pump wave of frequency $\omega_0$ is pulse-modulated, and the light pulses are transmitted to the fiber. A backscattered wave, having a frequency of approximately $\omega_0 - \Omega_B$, is then generated in the fiber due to SBS along the fiber's length. The backscattered wave is detected, and its frequency is instantaneously monitored as a function of time, following each transmitted pulse. If the fiber is exposed to uniform environmental conditions throughout its length, the detected wave frequency is constant, and shifted from that of the transmitted pulses by $\Omega_B$. If, however, the fiber is exposed, in some portion thereof, to some different conditions, e.g., strain different from that of other portions of the fiber, then the backscattered wave from that portion has frequency that deviates by some difference $\Delta\Omega$ from $\omega_0 - \Omega_B$. The magnitude of the frequency difference $\Delta\Omega$ is substantially proportional to the magnitude of the strain (or temperature) variation, typically by 0.5 GHz/% strain, and 1 MHz/° K. Further, the time gap $\Delta t$ between each transmitted pulse and the time when such a frequency change is detected with the backscattered wave, indicates the location, along the optical fiber, where the strain is applied: denoting the light wave group velocity in the fiber by $v_g$, the distance, along the fiber, from the end of the fiber to that location is $\frac{1}{2}\Delta t \cdot v_g$. Thus, by mapping the magnitude of the backscattered wave as a function of both time and frequency, the position and magnitude of strain (and temperature) variance is detected.

In Brillouin optical time domain analysis (BOTDA), a pump light wave is transmitted from one end of the fiber, while counter-propagating probe waves, typically substantially weaker than the pump waves, are transmitted from the other end of the optical fiber. The pump wave amplifies the probe waves having the frequencies that match the local Brillouin frequency shift in the fiber. The position-dependent frequency shift of the probe wave is then detected in a similar manner to the description relating to BOTDR above, through mapping the magnitude of the amplified probe as a function of both time and frequency.

In Brillouin optical correlation-domain analysis (BOCDA), a continuous, constant-magnitude pump wave is transmitted into an optical fiber from one end, and a continuous, constant-magnitude probe wave is transmitted into the optical fiber from the opposite end, and in the opposite direction to the pump wave. The frequencies of the two waves, which are nominally $\Omega_B$ apart, are synchronously modulated by a common sine wave. Due to the modulation, the frequency difference between the two counter-propagating waves remains stationary only at particular fiber locations, known as correlation peaks, whereas the frequency difference elsewhere is oscillating. Consequently, effective SBS amplification, and hence localized measurement, is restricted to the location, along the fiber, where correlation peaks occur.

SUMMARY

Aspects of the invention, in some embodiments thereof, relate to distributed sensing using an optical fiber. More specifically, aspects of the invention, in some embodiments thereof, relate to methods and devices that employ stimulated Brillouin scattering in optical fibers.

According to an aspect of some embodiments, there is provided a method for distributed sensing of one or more measurable parameters of an optical fiber. The method comprising generating a first pump light wave having a frequency centered at $\omega_0$; modulating the first pump light wave at a rate higher than about 1 GHz and lower than about 100 GHz, and the modulation is frequency modulation or phase modulation to obtain a first modulated pump light wave; transmitting the first modulated pump light wave into the optical fiber through a first end thereof; receiving at an end of the optical fiber a scattered light wave signal with a frequency approximately equal to $\omega_0+\Omega_B+\omega_{bir}$ or $\omega_0+\Omega_B-\omega_{bir}$ or $\omega_0-\Omega_B+\omega_{bir}$ or $\omega_0-\Omega_B\omega_{bir}$, wherein $\Omega_B$ is a Brillouin frequency shift of the optical fiber, and $\omega_{bir}$ is a birefringence frequency difference in the optical fiber; monitoring at least the frequency of the received light wave signal; and calculating from the monitored frequency of the received light wave signal a magnitude of a sensed measurable parameter of the optical fiber. In some embodiments, the rate of modulating the first pump light wave may be higher than about 2 GHz. In some embodiments, the rate of modulating the first pump light wave is higher than about 5 GHz. In some embodiments, the first pump light wave may be modulated by an anharmonic modulation signal in the modulating step. In some embodiments, the measurable parameters may be selected from the group consisting of strain and temperature. In some embodiments, the optical fiber may be deployed so as to interface a monitored object, at one or more locations along the length of the optical fiber. In some embodiments, the optical fiber interfaces the monitored object by mechanical contact. In some embodiments, the optical fiber interfaces the monitored object by thermal contact. In some embodiments, the monitored light wave signals may be generated within the optical fiber by stimulated Brillouin scattering of the first pump light wave transmitted into the optical fiber. In some embodiments, the first pump light wave may comprise at least one pulse of light, and the modulating step may comprise modulating the light frequency to vary within a range $$\left(\omega_0 - \frac{\Delta\omega}{2}, \omega_0 + \frac{\Delta\omega}{2}\right)$$

during the one or more pulse periods, and wherein $$\frac{\Delta\omega}{2\pi}$$

is greater than about 1 GHz and lower than about 100 GHz. In some embodiments, the light frequency may be varied linearly between $$\omega_0 - \frac{\Delta\omega}{2} \text{ and } \omega_0 + \frac{\Delta\omega}{2}$$

during the pulse periods. In some embodiments, the pulses of light may comprise a multiplicity of pulses of light, having a fixed pulse width and having a fixed time interval between consecutive pulses. In some embodiments, the monitoring step may include measuring a time of arrival of the received light wave signal. In some embodiments, the calculating step may include calculating a distance of a sensed location along the optical fiber using the monitored time of arrival. In some embodiments, the receiving step may comprise filtering the received light wave signal in a matched filter, thereby obtaining a pulse corresponding to the received light wave signals and having a pulse width shorter than the pulse width of the at least one pulse of the pump light wave. In some embodiments, following the step of generating a first pump light wave, the method may further comprise generating a generic random signal having a frequency centered substantially between 1 GHz and 100 GHz, and generating a first random signal by delaying the generic random signal by a time delay $\Delta T_1 \geq 0$. In some embodiments, the phase of the first pump light wave may be modulated by the first random signal. In some embodiments, following the step of generating a first pump light wave, the method may further include generating a probe light wave having a frequency centered at $\omega_1$, wherein $\omega_1$ is controllably tunable and shifted from $\omega_0$ by approximately $\Omega_B$, $\Omega_B$ being a Brillouin frequency shift of the optical fiber, and transmitting the probe light wave into the optical fiber through a second end thereof. In some embodiments, following the generation of a probe light wave and prior to transmitting the probe light wave, the method may further include generating a second random signal by delaying the generic random signal by a time delay $\Delta T_2 \geq 0$. The method may further include modulating the phase of the probe light wave by the second random signal. In some embodiments, the generic random signal may be a binary pseudo-random bit sequence signal comprising sequences of length M and bit duration T, assuming values of "0" and "1" with equal probabilities. In some embodiments, a "0" of the first random signal modulating the phase of the first pump light wave, does not vary the phase of the first pump light wave, and a "1" of the first random signal varies the phase by it radians. In some embodiments, a "0" of the second random signal modulating the phase of the probe light wave, does not vary the phase of the probe light wave, and a "1" of the second random signal varies the phase by $\pi$ radians. In some embodiments, the length M of the binary pseudo random bit sequence may be greater than about $2^{15}$. In some embodiments, the length M of the binary pseudo random bit sequence is greater than about $2^{22}$. In some embodiments, the bit time duration T may be varied to affect a scan of a sensed location along the optical fiber and a distance of a sensed location from an end of the optical fiber is calculated using a value of T. In some embodiments, the pseudo-random bit sequence length M may be varied to affect a scan of a sensed location along the optical fiber and a distance of a sensed location from an end of the optical fiber is calculated using a value of M. In some embodiments, at least one of the time delays $\Delta T_1$ and $\Delta T_2$ may be varied to affect a scan of a sensed location along the optical fiber and a distance of a sensed location from an end of the optical fiber is calculated using values of $\Delta T_1$ and $\Delta T_2$. In some embodiments, the optical fiber may be a polarization maintaining optical fiber. In some embodiments, prior to transmitting the first pump light wave, the method may further comprise polarizing the first pump light wave along a pre-selected first polarization direction $\vec{r}$. In some embodiments, the first polarization direction $\vec{r}$ may be along a principal axis $\vec{x}$ of the polarization maintaining optical fiber. In some embodiments, following generating a first pump light wave, the method may further comprise generating a generic random signal having a frequency centered substantially between 1 GHz and 100 GHz, and generating a first random signal by delaying the generic random signal by a time delay $\Delta T_1 \geq 0$, wherein modulating the first pump light wave may comprise modulating the phase of the first pump light wave by the first pseudo-random signal. In some embodiments, following generating a first random signal the method may further comprise: generating a second pump light wave having a frequency of $\omega_1$, wherein $\omega_1$ is controllably tunable and shifted from $\omega_0$ by approximately $\Omega_B$, $\Omega_B$ being a Brillouin frequency shift of the optical fiber; generating a second random signal by delaying the generic random signal by a time delay $\Delta T_2 \geq 0$; modulating the phase of the second pump light wave by the second pseudo-random signal; polarizing the second pump light wave along the pre-selected first polarization direction of the first pump light wave $\vec{r}$; and transmitting the second pump light wave into the optical fiber through a second end thereof. In some embodiments, following transmitting the second pump light wave the method may further comprise: generating a probe light wave having a frequency of $\omega_2$, wherein $\omega_2$ is controllably tunable and shifted from $\omega_0$ by approximately $\omega_{bir}$, $\omega_{bir}$ being a birefringence frequency difference in the optical fiber; polarizing the probe light wave along a second polarization direction substantially different from the first polarization direction of the first pump light wave $\vec{r}$; and transmitting the probe light wave into the optical fiber through the first end thereof, wherein receiving at an end of the optical fiber of a scattered light wave signal, comprises receiving at the first end of the optical fiber a scattered light wave signal, having a frequency approximately equal to $\omega_{sig}$, and $\omega_{sig}$ is shifted from the frequency $\omega_2$ of the probe signal by approximately $\Omega_B$, $\Omega_B$ being a Brillouin frequency shift of the optical fiber. In some embodiments, the second polarization direction may be along a second principal axis $\vec{y}$ of the optical fiber. In some embodiments, the method may further comprise modulating one or more pump light waves by pulse modulation. In some embodiments, the method may further comprise modulating the probe light wave by pulse modulation. In some embodiments, the method may further comprise synchronizing the pulse modulation of the pump light waves, the pulse modulation of the probe light waves and one or more phase modulations modulating a pump light wave or the probe light wave.

According to an aspect of some embodiments, there is provided a device for distributed sensing of one or more measurable parameters of an optical fiber, the device comprises a frequency modulator for modulating a pump light wave in accordance with the methods described above.

According to an aspect of some embodiments, there is provided a device for distributed sensing of one or more measurable parameters of an optical fiber, comprising a phase modulator for modulating a pump light wave in accordance with a the methods described above According to an aspect of some embodiments, there is provided a device for distributed sensing of an optical fiber, configured for transmitting a modulated pump light wave into the optical fiber through an end thereof, and for receiving a scattered light wave signal from an end thereof. The device comprising: a light source configured for generating a coherent light wave having a frequency of $\omega_0$; functionally associated with the light source, a modulator configured for modulating the phase or the frequency of the coherent light wave, thereby generating a modulated pump light wave; and functionally associated with the modulator, a modulation signal generator configured for generating a modulation signal to modulate the phase or the frequency of the coherent light source by the modulator, wherein the modulation signal generated by the modulation signal generator has a frequency greater than 1 GHz and smaller than 100 GHz. In some embodiments the modulation signal generated by the modulation signal generator may be an anharmonic signal. In some embodiments the modulator may be a frequency modulator. In some embodiments the modulator may be a phase modulator. In some embodiments the device may further comprise a pulse modulator functionally associated with the light source generator for at least one pulse of the pump light wave, wherein the frequency modulator modulates the frequency of the pump light wave to vary substantially linearly within a range $$\left(\omega_0 - \frac{\Delta\omega}{2}, \ \omega_0 + \frac{\Delta\omega}{2}\right)$$

during the at least one pulse period, and wherein $$\frac{\Delta\omega}{2\pi}$$

is greater than about 1 GHz and lower than about 100 GHz. In some embodiments the modulation signal generated by the modulation signal generator may be a random signal. In some embodiments the modulation signal generated by the modulation signal generator, is a pseudo-random bit sequence signal. In some embodiments the optical fiber may be a polarization maintaining optical fiber.

The spatial resolution in known methods employing SBS for distributed sensing may be limited by the lifetime of the acoustic phonons engaged in the Brillouin scattering. The phonons typical life time τ is τ=6 nsec, corresponding to a spatial resolution Rs of about 1 m. By limited spatial resolution it is meant that a variance in strain or temperature along the optical fiber, with spatial extent that is smaller than the resolution limit, can not be detected (or is hard to detect). An attempt to increase spatial resolution, for example by decreasing pulse widths in BOTDR or BOTDA below such time scales, yields a significant spread in the value of $\Omega_B$ and consequently loss of specificity of a local strain-induced or temperature-induced frequency shift. In BOCDA a length of a portion of the optical fiber which is sensed can be arbitrarily decreased by decreasing the width of the correlation peak. However the unambiguous measurement range of BOCDA is restricted to the separation between periodic correlation peaks, which is typically several hundreds times the spatial resolution. Hence when simple sine-wave frequency modulation is used in BOCDA, tight trade-offs prevail between the measurement range and spatial resolution.

Thus, known methods for distributed sensing which employ SBS in optical fibers may be subjected to intrinsic limitations on spatial resolution that these methods may achieve. These intrinsic limitations result from the life time of phonons engaged in SBS in an optical fiber. In some such methods the limit on spatial resolution is absolute, namely spatial resolution can not be substantially increased beyond some absolute value; in other methods phonons life time imposes a trade off such that enhancing spatial resolution results in depreciation of e.g. spatial range of measurement.

According to an aspect of some embodiments of the invention there is provided a method for distributed sensing of one or more measurable parameters of a monitored object using an optical fiber. The monitored object may be the optical fiber itself, the cable in which the optical fiber is contained, an object physically or thermally affecting the optical fiber, or the like. In some embodiments, the method may utilize an optical fiber deployed so that the optical fiber interfaces the monitored object at least in one or more locations along the optical fibers length.

The method may include generating a first pump light wave having a frequency centered at $\omega_0$ and modulating the first pump light wave at a rate higher than about 1 GHz and lower than about 100 GHz, wherein the modulation may be frequency modulation or phase modulation. The pump light may then be transmitted into the optical fiber through a first end thereof. The method may further comprise receiving at one or two ends of the optical fiber light wave signals with a frequency approximately equal to $\omega_{sig}$, wherein $\omega_{sig}$ may be $\omega_0-\Omega_B-\omega_{bir}$, $\omega_0-\Omega_B+\omega_{bir}$, $\omega_0+\Omega_B-\omega_{bir}$, or $\omega_0+\Omega_B+\omega_{bir}$. $\Omega_B$ is a Brillouin frequency shift of the optical fiber, and $\omega_{bir}$ is a birefringence frequency difference in the optical fiber.

The method may further comprise monitoring at least the frequency of the light wave signals. Then, a magnitude of a sensed measurable parameter may be determined from the monitored frequency of the light wave signal A pump light wave modulated at a rate larger than 1 GHz is varied over time constants that are smaller than the typical life time of about 6 nSec of phonons engaged in SBS in standard optical fibers. In some embodiments, modulating the frequency of the pump light wave at a rate higher than 1 GHz, may allow the restriction of the spatial region of SBS generation to a portion of the optical fiber that is smaller than the portion of an optical fiber in which SBS is generated by current methods for distributed sensing. In other words, modulating the frequency of the pump light wave at a rate higher than 1 GHz, may allow for reducing the spatial range in which the required parameters are measured and consequently may allow improving the spatial resolution of the measurement. Yet, in some embodiments, and according to the teachings herein, such modulation may allow exciting and maintaining SBS-assisting phonons for time periods that exceed the phonons life time.

Further, in some embodiments, modulating the phase of the pump light wave at a rate higher than 1 GHz, may allow the restriction of the spatial region of SBS generation to a portion of the optical fiber that is smaller than the portion of an optical fiber in which SBS is generated by current methods. In other words, modulating the phase of the pump light wave at a rate higher than 1 GHz, may allow reducing the spatial range in which the required parameters are measured and consequently may allow improving the spatial resolution of the measurement. Yet, in some embodiments, and according to the teachings herein, such modulation allows exciting and maintaining SBS-assisting phonons for time periods that exceed the phonons life time.

BRIEF DESCRIPTION OF THE FIGURES

Some embodiments of the invention are described herein with reference to the accompanying figures. The description, together with the figures, makes apparent to a person having ordinary skill in the art how embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DETAILED DESCRIPTION

The principles, uses and implementations of the teachings herein may be better understood with reference to the accompanying description and figures. Upon perusal of the description and figures present herein, one skilled in the art is able to implement the invention without undue effort or experimentation.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

As discussed above, current methods for distributed sensing using an optical fiber are subjected to limitations on the spatial resolution such methods provide. A technical solution to this problem comprises the distributed sensing with higher spatial resolution than resolution enabled through prior art methods. In some embodiments, a pump light wave pulse is frequency-modulated at a frequency, for example, of about or above 1 GHz, and the measurement comprises comparing the pump wave and a back-scattered wave. In some embodiments at least a pump light wave or a probe light wave is phase-modulated using random or pseudo-random modulation in high frequency, for example frequency of about or above 1 GHz. The measurement may comprise comparing the pump light wave and a forward-scattered probe light wave. In yet further embodiments, which may be used in polarization-maintaining optical fiber, two pump light waves and a probe light wave are phase-modulated using random or pseudo-random modulation as described above, and the measurement comprises comparing the two pump waves and a back-scattered scattered probe wave.

Figure 1B:
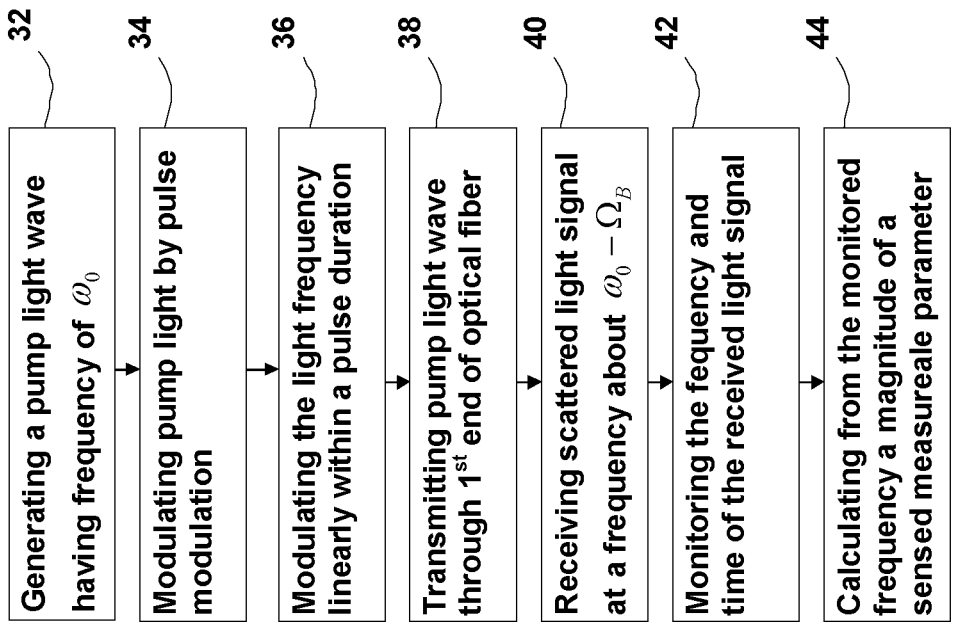
FIGS. 1A and 1B schematically illustrate two methods, respectively, for distributed sensing using an optical fiber, in accordance with some embodiments of the disclosure.
Figure 1A:
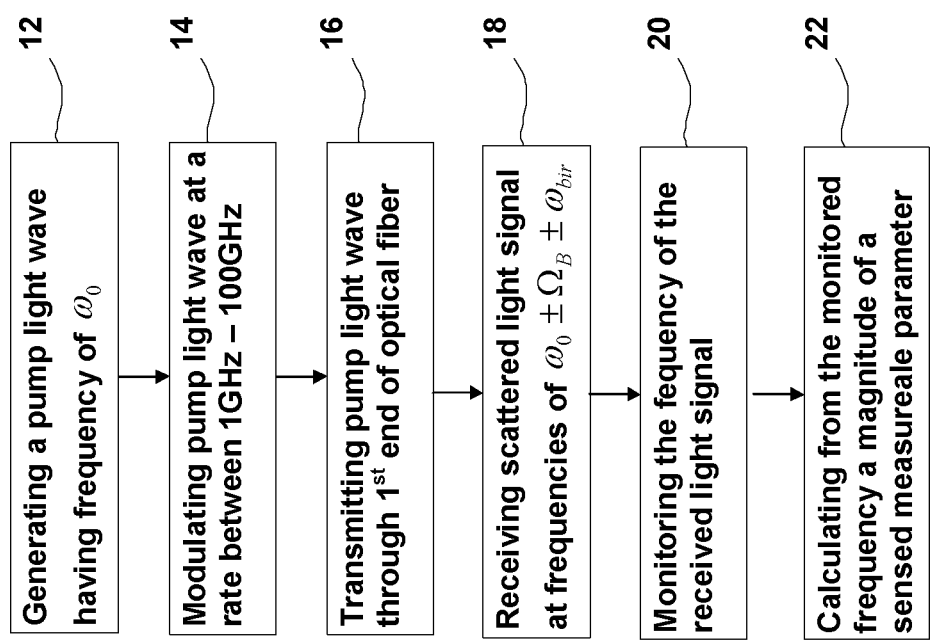

Referring now to FIG. 1A, according to an aspect of some embodiments of the invention there is provided a method for distributed sensing of one or more measurable parameters associated with an optical fiber.

The method may comprise step 12 of generating a first light wave having a frequency centered at $\omega_0$.

The method may further comprise step 14 of modulating the first light wave at a rate greater than about 1 GHz and lower than about 100 GHz, where the modulation may be frequency modulation or phase modulation, thereby obtaining a first modulated pump light wave.

The method may further comprise step 16 of transmitting the first modulated pump light wave into the optical fiber through a first end thereof.

The method may further comprise step 18 of receiving at an end of the optical fiber a scattered light wave signal with a light frequency approximately equal to $\omega_0-\Omega_B-\omega_{bir}$ or $\omega_0-\Omega_B+\omega_{bir}$ or $\omega_0+\Omega_B-\omega_b$, or $\omega_0+\Omega_B+\omega_{bir}$, $\Omega_B$ being a Brillouin frequency shift of the optical fiber, and $\omega_{bir}$ being a birefringence frequency difference in the optical fiber. It will be noted that if the optical fiber is not a polarization maintaining optical fiber, then $\omega_{bir}$ is equal to zero, thus leaving only the light frequencies of $\omega_0-\Omega_B$ and $\omega_0+\Omega_B$.

The method may further comprise step 20 of monitoring at least the frequency of the received light wave signal.

The method may further comprise step 22 of calculating from the monitored frequency of the light wave signal a magnitude of a sensed measurable parameter.

Pulses of Frequency-Modulated Light Wave

Referring now to FIG. 1B, according to an aspect of some embodiments of the invention there is provided a method for distributed sensing of one or more measurable parameters of a monitored object using an optical fiber:

The method may comprise step 32 of generating a light wave having a frequency centered at $\omega_0$.

The method may further comprise step 34 of modulating the light wave by pulse modulation, thereby generating light pulses. Generally, the light pulses have pulse width greater than the typical phonons life time of about 6 nSec.

The method may further comprise step 36 of modulating the light frequency of the light wave so that the light frequency is varied linearly within a range $$\left(\omega_0 - \frac{\Delta\omega}{2}, \omega_0 + \frac{\Delta\omega}{2}\right)$$

during a single pulse, wherein $$\frac{\Delta\omega}{2\pi}$$

is higher or equal to about 1 GHz and smaller or equal to 100 GHz, thereby generating a modulated pump light wave.

The method may further comprise step 38 of transmitting the modulated pump light wave pulses to the optical fiber through a first end thereof.

The method may further comprise, following transmission of each of the pump light wave pulses, step 40 of receiving at the first end of the optical fiber, a scattered light wave signal with light frequency approximately equal to $\omega_0-\Omega_B$, $\Omega_B$ being a Brillouin frequency shift of the optical fiber.

The method may further comprise step 42 of monitoring the time of arrival and the light frequency of the received light wave signals. The time of arrival is the time difference between the transmission of pulse of a pump light wave and the receiving of the corresponding scattered light wave signal.

The method may further comprise step 44 of calculating a distance of a sensed location along the optical fiber using the monitored time of arrival, and calculating a magnitude of a sensed measurable parameter associated with the optical fiber using the monitored light frequency of the light wave signals.

As discussed above, in known methods, such as BOTDR, that employ light pulses and generation of SBS for distributed sensing, spatial resolution is limited by the pulse width, i.e., the time duration of the pulses. Pulse duration in turn is limited by the typical life time of phonons engaged with the SBS: if the pulse duration is smaller than the phonons life time, such phonons are relatively weak or not generated at all, and SBS, substantially, does not occur. The method according to the teachings herein overcomes this limitation by modulating the light wave frequency of transmitted light pulses. In other words, modulating the light frequency enables transmission of pulses having pulse width longer than the life time of phonons, and yet enhancing the spatial resolution.

In some embodiments a wave form of a single transmitted pulse of light may be mathematically described as $$V(t) \propto \cos\left[2\pi f_0 t + (2\pi B/T)t^2 - \pi Bt\right] \cdot rect(t/T)$$

wherein $f_0$ is the center frequency of the light wave, $2\pi f_0 = \omega_0$, and B is the width of the scanned frequency range. In other words the frequency may be varied linearly from $f_0 - B/2$ to $f_0 + B/2$, and in angular frequency terms from $\omega_0 - \Delta\omega/2$ to $\omega_0 + \Delta\omega/2$ where $\Delta\omega/2\pi = B \cdot rect(x)$ is 1 for x between 0 and 1, and 0 elsewhere. According to the teachings herein, B may be selected so that the width of the scanned frequency range is greater than about 1 GHz and smaller than about 100 GHz.

Figure 1C:
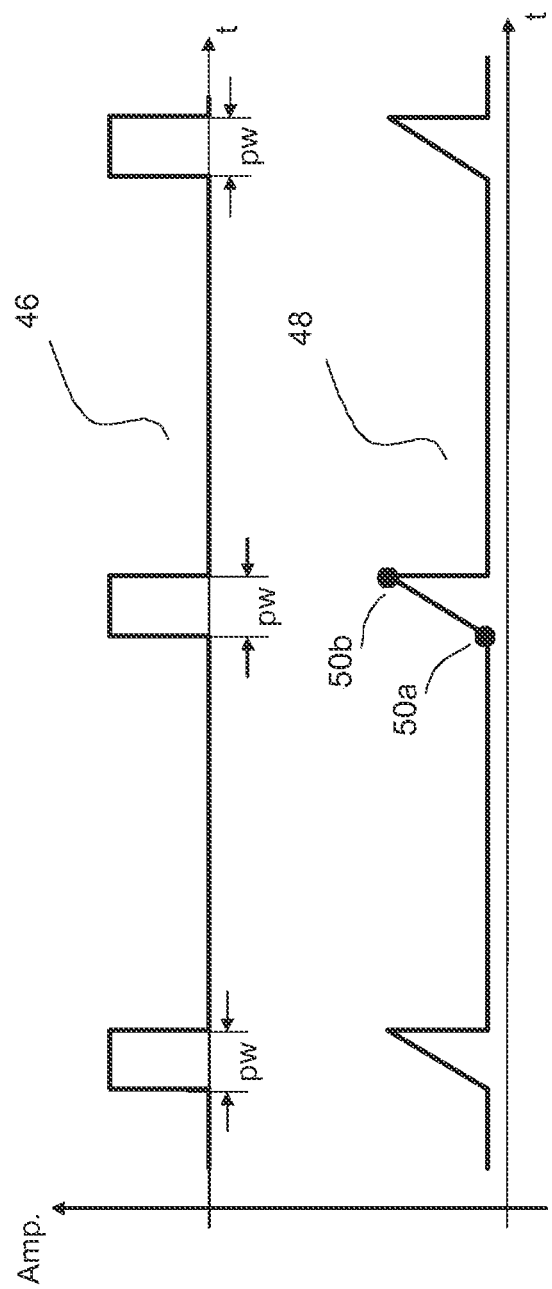
FIG. 1C schematically depicts an anharmonic modulating signal for frequency-modulating a pump light wave in accordance with the method of FIG. 1B.

FIG. 1C schematically depicts a pulse modulating signal 46 for pulse-modulating the pump light wave, to obtain pulses having a pulse width of pw. A saw-tooth modulating signal 48 is synchronized with pulse modulating signal 46. Saw-tooth modulating signal 48 is an exemplary anharmonic modulation signal for frequency-modulating the pump light wave in accordance with the teaching herein. Saw-tooth modulating signal 48 has a linear portion, extending during the pulse duration from a point 50a at the start of the pulse to a point 50b at the end of the pulse. In some embodiments, saw-tooth modulating signal 48 modulates the pump light wave frequency so that at point 50a the light frequency is $\omega_0 - \Delta\omega/2$ and at point 50b the light frequency is $\omega_0 + \Delta\omega/2$, and the light frequency varies linearly during the pulse duration in accordance with saw-tooth modulating signal 48. By modulating the light wave as described above, the pump light wave is frequency-modulated at a rate that is greater than about 1 GHz and smaller than about 100 GHz.

In some embodiments the method of FIG. 1C further comprises filtering the received light wave signal using a matched filter, thereby obtaining a pulse corresponding to the received light wave signals and having a pulse width shorter than the pulse width of the pump light pulses. In some embodiments, filtering the received signals in a matched filter comprises autocorrelating the received light wave signal and the light wave of the pump light wave. As is well known in the art, filtering a pulsed wave, having a frequency varied linearly in time as described above, in a matched filter, obtains a pulse response and the obtained pulse has typical pulse width of about 1/B. For a scanned frequency range selected so that B is greater than 1 GHz, a pulse obtained from a matched filter as described above has a pulse width smaller than 1 nSec. In terms of spatial resolution of distributed sensing using an optical fiber, a pulse having a pulse width of about 1 nSec enables spatial resolution of about 20 cm, i.e., information related to locations along the fiber which are about 20 cm apart can be received separately. By transmitting a pulse having a pulse width greater than the phonons life time of about 6 nSec, SBS is properly generated in the optical fiber, and specificity of the Brillouin frequency shift is not compromised. By obtaining a pulse corresponding to the received (scattered) light wave signal and having a pulse width smaller than the transmitted pulse width, spatial resolution is enhanced.

In some embodiments, sensing a measurable parameter such as temperature or strain, and particularly sensing a local variance in such a measurable parameter, comprises monitoring the time of arrival and the light frequency of the received light wave signals. As discussed above, received light wave signals have frequencies approximately equal to $\omega_0-\Omega_B$ where $\Omega_B$ is a Brillouin frequency shift characteristic to the optical fiber. If a portion of the optical fiber is exposed for example to a strain variation, the scattered light wave signal associated with that portion of the optical fiber has frequency different from $\omega_0-\Omega_B$ by some frequency difference $\Delta\Omega$, wherein the magnitude of the frequency difference $\Delta\Omega$ is substantially proportional to the magnitude of the strain variation. Further, the time difference $\Delta t$ between a transmitted pulse and the time when such a frequency change is detected at the received light wave signal, indicates the location, along the optical fiber, where strain is applied: denoting the light wave group velocity in the fiber by $v_g$, the distance, along the fiber, from the end of the fiber to that location is $\frac{1}{2}\Delta t \cdot v_g$. Thus, by mapping the magnitude of the backscattered wave as a function of both time and frequency, the position and magnitude of a sensed variance in a measurable parameter may be measured.

In some embodiments, the method further comprises transmitting a series of light pulses, having a fixed time interval between consecutive pulses and each pulse having a pulse width greater than about 6 nsec, wherein the light wave frequency within each light pulse is varied linearly between $\omega_0-\Delta\omega/2$ and $\omega_0+\Delta\omega/2$. Receiving light wave signals following the transmitted pulses, monitoring the frequency and time of arrival of such received light wave signals and calculating a distance of a sensed location along the optical fiber and a magnitude of a sensed measurable parameter, may be carried out substantially as described above.

Random Phase Modulation, Standard Optical Fibers

Figure 1D:
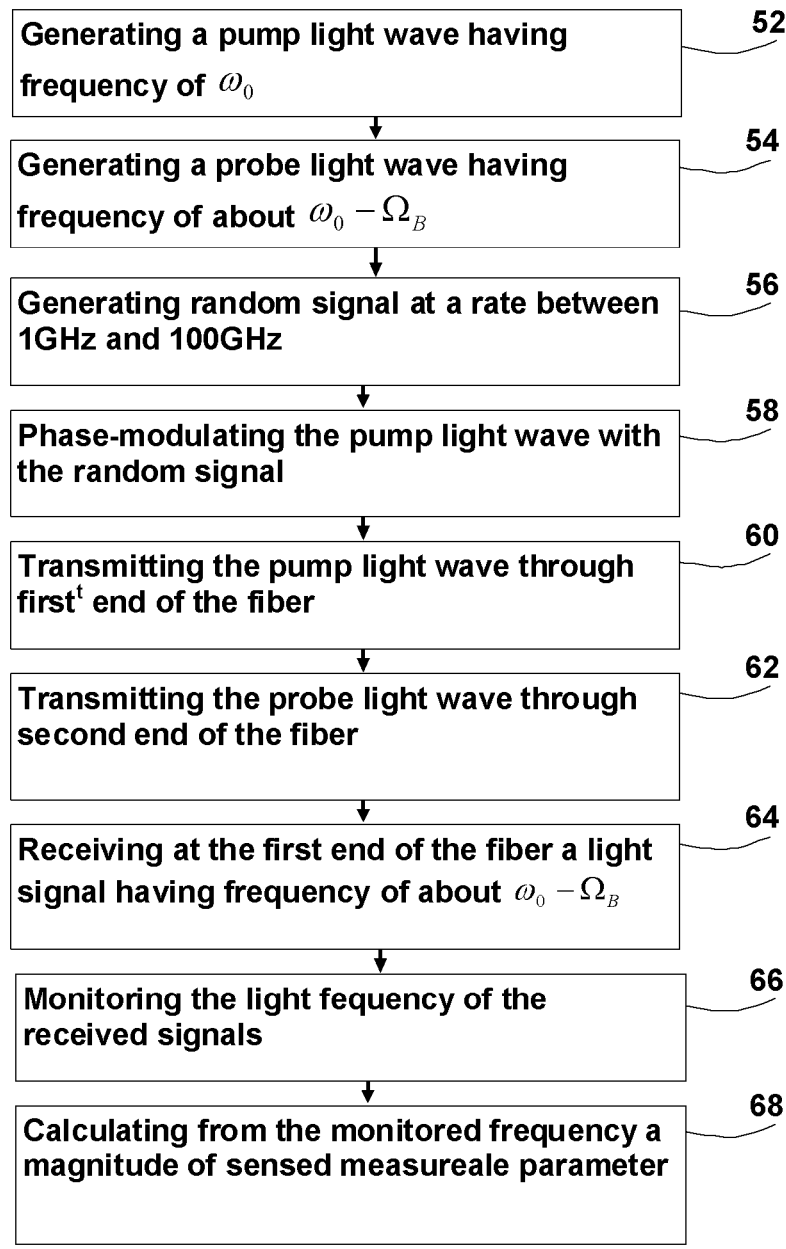
FIG. 1D schematically illustrates a method for distributed sensing using an optical fiber, in accordance with some embodiments of the disclosure.

Referring now to FIG. 1D, according to an aspect of some embodiments there is further provided a method for distributed sensing of one or more measurable parameters of a monitored object using an optical fiber:

The method may comprise step 52 of generating a first light wave having a frequency centered at $\omega_0$.

The method may further comprise step 54 of generating a probe light wave having a frequency of $\omega_1$, approximately equal to $\omega_0-\Omega_B$, $\Omega_B$ being a Brillouin frequency shift of the optical fiber.

The method may further comprise step 56 of generating at least a first random signal having a frequency centered substantially between 1 GHz and 100 GHz.

The method may further comprise step 58 of modulating the phase of at least the first light wave by the first random signal thereby generating a modulated pump light wave signal.

The method may further comprise step 60 of transmitting the modulated pump light wave into the optical fiber through a first end thereof.

The method may further comprise step 62 of transmitting the probe light wave into the optical fiber through a second end thereof.

The method may further comprise step 64 of receiving at the first end of the optical fiber scattered light wave signals with light frequency approximately equal to $\omega_0-\Omega_B$, $\Omega_B$ being a Brillouin frequency shift of the optical fiber.

The method may further comprise step 66 of monitoring the frequency of the light wave signals.

The method may further comprise step 68 of calculating from the monitored frequency of the light wave signal a magnitude of a sensed measurable parameter associated with the optical fiber.

In some embodiments the method further comprises pulse-modulating the pump light wave. In some embodiments the method further comprises pulse-modulating the probe light wave. By modulating one of the pump light wave and the probe light wave, or both, measurement accuracy may be increased. In some such embodiments signal to noise ratio of the measurement may be improved, as is explained further below.

Figure 2:
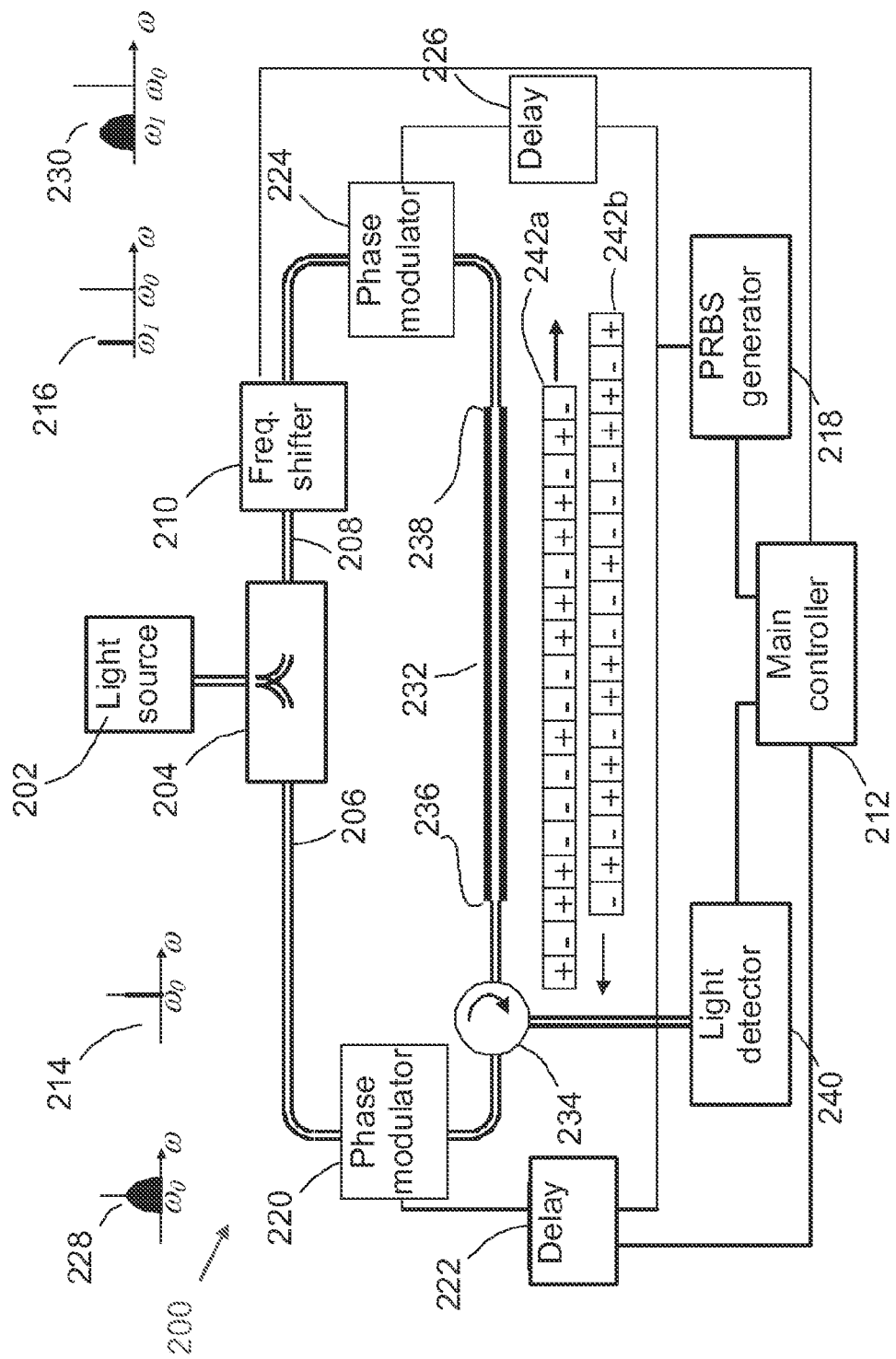
FIG. 2 schematically depicts a system configured to carry out distributed sensing using an optical fiber, in accordance with some embodiments of the disclosure.

Reference is now made to FIG. 2, depicting schematically an embodiment of a system 200. A coherent light source 202, such as a laser, generates a continuous light wave having a frequency of $\omega_0$. A splitter 204 is functionally associated with coherent light source 202. Splitter 204 splits the power of the generated light wave to a pump branch 206, thereby generating a pump light wave at a frequency $\omega_0$, and to a probe branch 208. A frequency shifter 210 is functionally associated with splitter 204 through probe branch 208. Frequency shifter 210 shifts the frequency $\omega_0$ of the continuous light wave by a frequency gap $\Omega$ to generate a probe light wave at a frequency $\omega_1=\omega_0-\Omega$. Frequency shifter 210 is functionally associated with a main controller 212, and is configured to vary the frequency gap $\Omega$ according to control signals from main controller 212.

Graph 214 schematically depicts the pump light wave in the spectral domain as a single spectral line at $\omega_0$. Graph 216 schematically depicts the probe light wave in the spectral domain as a single spectral line at $\omega_1$, $\omega_1$ is shifted from $\omega_0$ by $\Omega$.

A pseudo random binary sequence (PRBS) generator 218 is configured to generate a generic binary pseudo-random bit sequence having a length M and equal probabilities of "0" and "1" for every bit. The bit sequence is generated at a nominal rate higher than 1 GHz, in other words single bit duration T is smaller than 1 nSec and considerably smaller than 5 nsec. In some embodiments, the duration of a single bit is smaller than 0.5 nsec, and in some embodiments T is even smaller than 0.1 nsec.

A first phase modulator 220 on pump branch 206 is functionally associated with PRBS generator 218, through a first delay line 222. A second phase modulator 224, functionally associated with frequency shifter 210 on probe branch 208, is functionally associated with PRBS generator 218 through a second delay line 226. First delay line 222 delays the pseudo-random bit sequence generated by PRBS generator 218 by a tunable time delay $\Delta T_1$, thereby generating a first pseudo-random bit sequence. The first pseudo-random bit sequence controls first phase modulator 220 to modulate the phase of the pump light wave. A "0" symbol of the first pseudo-random bit sequence generates no phase shift of the pump light wave, whereas a "1" symbol generates a phase shift of $\pi$ radians. The same generic pseudo-random bit sequence generated by PRBS generator 218 is delayed by a constant time delay $\Delta T_2$ by second delay line 226, to generate a second pseudo-random bit sequence. The second pseudo-random bit sequence controls second phase modulator 224 to modulate the phase of the probe light wave: a "0" symbol generates no phase shift of the probe light wave, whereas a "1" symbol generates a phase shift of $\pi$ radians.

Graph 228 schematically depicts the pump light wave in the spectral domain following modulation by first phase modulator 220. The phase-modulated pump light wave has a broad spectrum, centered at $\omega_0$ and with a width that corresponds to the rate of the modulating bit sequence. The modulated probe light wave spectrum, schematically depicted on graph 230, is centered at $\omega_1$ and has a similar width to that of the pump light wave.

Main controller 212 is functionally associated with first delay line 222 and is configured to control first delay line 222 thereby tuning the delay $\Delta T_1$. A desired delay $\Delta T$ between the modulating signals of the pump light wave and the probe light wave is obtained by selecting $\Delta T_1$ so that $\Delta T_1 - \Delta T_2 = \Delta T$. By selecting $\Delta T_2 < \Delta T_1$, the modulation signal of the pump light wave is delayed relative to the modulation signal of the probe light wave, and by selecting $\Delta T_1 < \Delta T_2$, the modulation signal of the pump light wave is promoted (in time) relative to the modulation signal of the probe light wave. It is noted that the delays $\Delta T_1$, $\Delta T_2$ and $\Delta T$ do not affect the spectra of the pump and probe light waves. It will be appreciated that either first delay line 222 or second delay line 226 may be omitted, such that $\Delta T$ is determined by second delay line 226 or first delay line 222, respectively.

System 200 is further associated with optical fiber 232. In some embodiments optical fiber 232 is configured to be deployed and to interface, at one or more locations along the length of optical fiber 232, with a monitored object (not shown). The modulated pump light wave is transmitted, through a circulator 234, into optical fiber 232 through a first end 236, propagating thereby from first end 236 to a second end 238. The probe light wave is transmitted into optical fiber 232 through second end 238, thereby propagating in the opposite direction relative to the pump light wave, namely from second end 238 to first end 236.

Circulator 234 is functionally associated with first phase modulator 220, with first end 236 of optical fiber 232 and with a light signal detector 240. Circulator 234 is configured to allow the modulated pump light wave from first phase modulator 220 to first end 236 of optical fiber 232, and to disallow the same modulated pump light wave to light signal detector 240. Further, circulator 234 is configured to allow light signals from first end 236 of optical fiber 232 to light signal detector 240, and to disallow the same light signals to first phase modulator 220.

Light signal detector 240 is configured to detect light signals emitted from first end 236 of optical fiber 232. Such light signals are substantially spectral components of the forward-scattered probe light wave, propagating from second end 238 to first end 236, that are selectively amplified in optical fiber 232 by stimulated Brillouin scattering, as is further detailed below. Main controller 212 is functionally associated with light signal detector 240, to receive detected signals therefrom.

In operation, a pump light wave, having a center frequency $\omega_0$ and being phase-modulated by a first pseudo random bit sequence, propagates in optical fiber 232 from first end 236 to second end 238. Simultaneously, a probe light wave, at a center frequency $\omega_1$ (shifted from $\omega_0$ by a frequency gap $\Omega$) is transmitted into optical fiber 232 from second end 238, to propagate in the opposite direction to that of the pump light wave. The probe light wave is phase-modulated by a second pseudo-random bit sequence, that is delayed or promoted in time relative to the first pseudo random bit sequence, according to the relative magnitudes of the delays $\Delta T_1$ and $\Delta T_2$ (namely according to the sign of $\Delta T$). Yet, apart from the relative delay between the first and second pseudo-random bit sequences, the two bit sequences are identical.

Rows 242a and 242b are exemplary sequences of the phase shift of the pump light wave and the probe light wave, respectively, as a function of position along optical fiber 232 at an arbitrary point in time. A "−" indicates a zero phase shift and a "+" indicates a phase shift of $\pi$ rad. The sequences in rows 242a and 242b are substantially identical to related portions of the first pseudo random bit sequence and the second pseudo random bit sequence, respectively, as a function of time. Although the sequences shown in rows 242a and 242b are depicted in opposing directions for explanatory purposes, it can be seen that they are identical. As time progresses, the pump light wave propagates from first end 236 to second end 238, and the probe light wave propagates in the opposite direction, and thereby the sequence of phase shifts of each of the light wave propagates, substantially at the group velocity $v_g$ of light wave in the fiber, as is indicated by the respective arrows next to the rows 242a and 242b.

Figure 3:
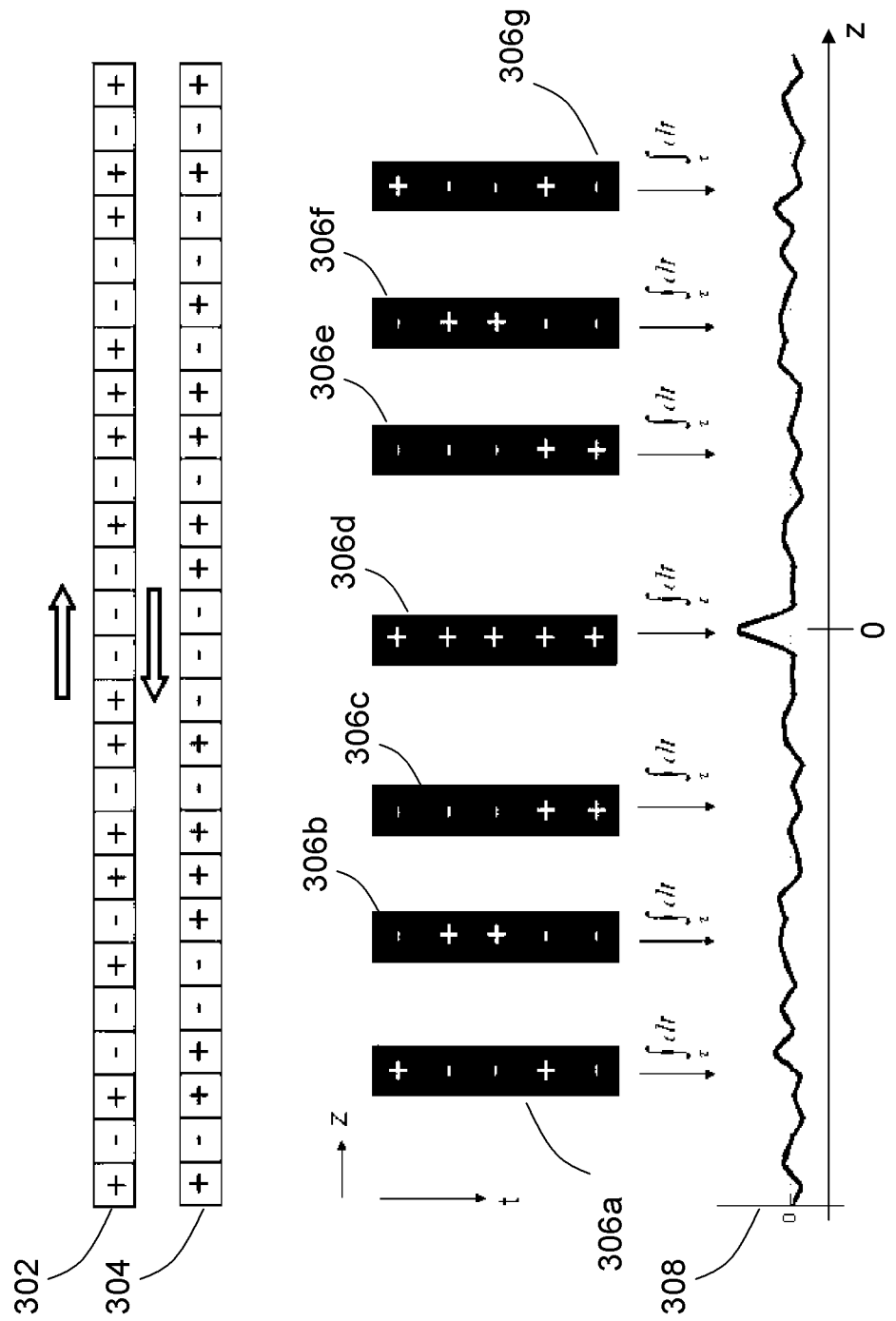
FIG. 3 schematically depicts two counter-propagating light waves in an optical fiber, phase-modulated by a binary pseudo-random bit sequence, and corresponding formation of a correlation peak in the optical fiber, in accordance with some embodiments of the disclosure.

FIG. 3 schematically depicts the combined effect of the counter-propagating pump light wave and probe light wave in an optical fiber. Rows 302 and 304 in FIG. 3 are exemplary sequences of the phase shift of the pump light wave and the probe light wave, respectively, as a function of position along the optical fiber at an arbitrary point in time. Position along the optical fiber is indicated by axis z. In this example the phase modulation signals of the pump light wave and the probe light wave are synchronized, with no relative time delay therebetween, so that the two waves are of equal phases at the respective entry points to the optical fiber. Consequently, in the vicinity of the middle of the optical fiber (indicated by z=0), at equal distances from the two ends, a correlation peak is formed: the pump light wave and probe light wave are correlated, and their phase difference is constant. The width of the correlation peak is in the order of $\Delta z = \frac{1}{2} v_g T$, $v_g$ being the group velocity of light in the fiber.

Sequences 306a-306g are the resulting phase differences between the pump light wave and the probe light wave, as a function of time, in seven arbitrary points along the optical fiber, wherein 306d relates to the middle of the fiber (z=0), or its vicinity. A "+" indicates some arbitrary phase difference $\phi$, and a "−" indicates a phase difference $\phi + \pi$. Only the sequence at the middle of the fiber (z=0) indicates a constant phase difference between the pump and the probe light waves, while in all other points the phase difference alternates as a function of time, due to the randomness of the bit sequence that modulates the two waves.

The acoustic field is generated if the acoustic field driving force persists over time intervals larger than the phonons life time. Because the phase match between the pump and the probe light waves is steady at the correlation peak, and particularly lasts longer than phonons life time, SBS-related phonons are generated at the location of the correlation peak. In all other locations, the driving force for the acoustic field is randomly alternating in sign on every bit duration T, which is much smaller than the phonons life time. Thus, in all locations except the location of the correlation peak, the acoustic field magnitude averages out to a zero expectation value, and the SBS interaction outside the location of the correlation peak is substantially inhibited. Graph 308 depicts schematically the magnitude of the acoustic field inside the optical fiber, obtained by integration over time of the driving force of the acoustic field at every point z. The integration time window is on the order of magnitude of the phonons life time, which is considerably larger than the bit time duration T. At the correlation peak location, shown at z=o, the acoustic field is maximal, and in all other locations the acoustic field is alternating at a low magnitude. As a result, effective SBS, and consequential amplification of the probe light wave, can occur only at the region of the correlation peak—at z=0 in the example of FIG. 3—over a distance that can be controllably increased or decreased by tuning the bit time duration T. It is noted that actual amplification of the probe light wave can occur only if, in the location of the correlation peak, the frequencies of the pump light wave and the probe light wave differ by exactly $\Omega_B$, the local Brillouin frequency shift of that location of the optical fiber.

Referring now back to FIG. 2, sensing of the local Brillouin frequency shift along the entire length of optical fiber 232 is carried out for example according to the following method: main controller 212 tunes first delay line 222 to affect a delay $\Delta T_1$, thereby setting the magnitude and sign of the relative delay $\Delta T$ between the first pseudo-random bit sequence and the second pseudo random bit sequence. The relative delay $\Delta T$ sets the location of the correlation peak along optical fiber 232. For example, when $\Delta T$ is positive, the correlation peak is closer to first end 236. When $\Delta T=0$ the correlation peak is substantially at the middle of optical fiber 232, and when $\Delta T$ is negative, the correlation peak is closer to second end 238. By changing $\Delta T$ from a suitable negative value to a suitable positive value, the position of the correlation peak is made to scan a required portion of optical fiber 232, for example the entire length of optical fiber 232.

At every position of the correlation peak along optical fiber 232, main controller 212 controls frequency shifter 210 to vary the frequency shift $\Omega$ within a selected range $\Delta\omega$. The $\Delta\omega$ range includes the nominal value of the Brillouin frequency shift $\Omega_B$ of optical fiber 232, that is to say the Brillouin frequency shift of optical fiber 232 at normal conditions. The range $\Delta\omega$ is further selected so as to include a Brillouin frequency shift that may result from an expected variance from normal conditions in a measurable parameter (such as strain or temperature), in optical fiber 232. During a scan of the range $\Delta\omega$, when the difference $\Omega$ between the frequencies of the pump light wave and the probe light wave is equal to the local Brillouin frequency shift of optical fiber 232 at the position of the correlation peak, the probe light wave is amplified, generating a consequent light signal at first end 236 of optical fiber 232. Such a light signal at first end 236 is detected by light signal detector 240, and received by main controller 212.

Figure 4:
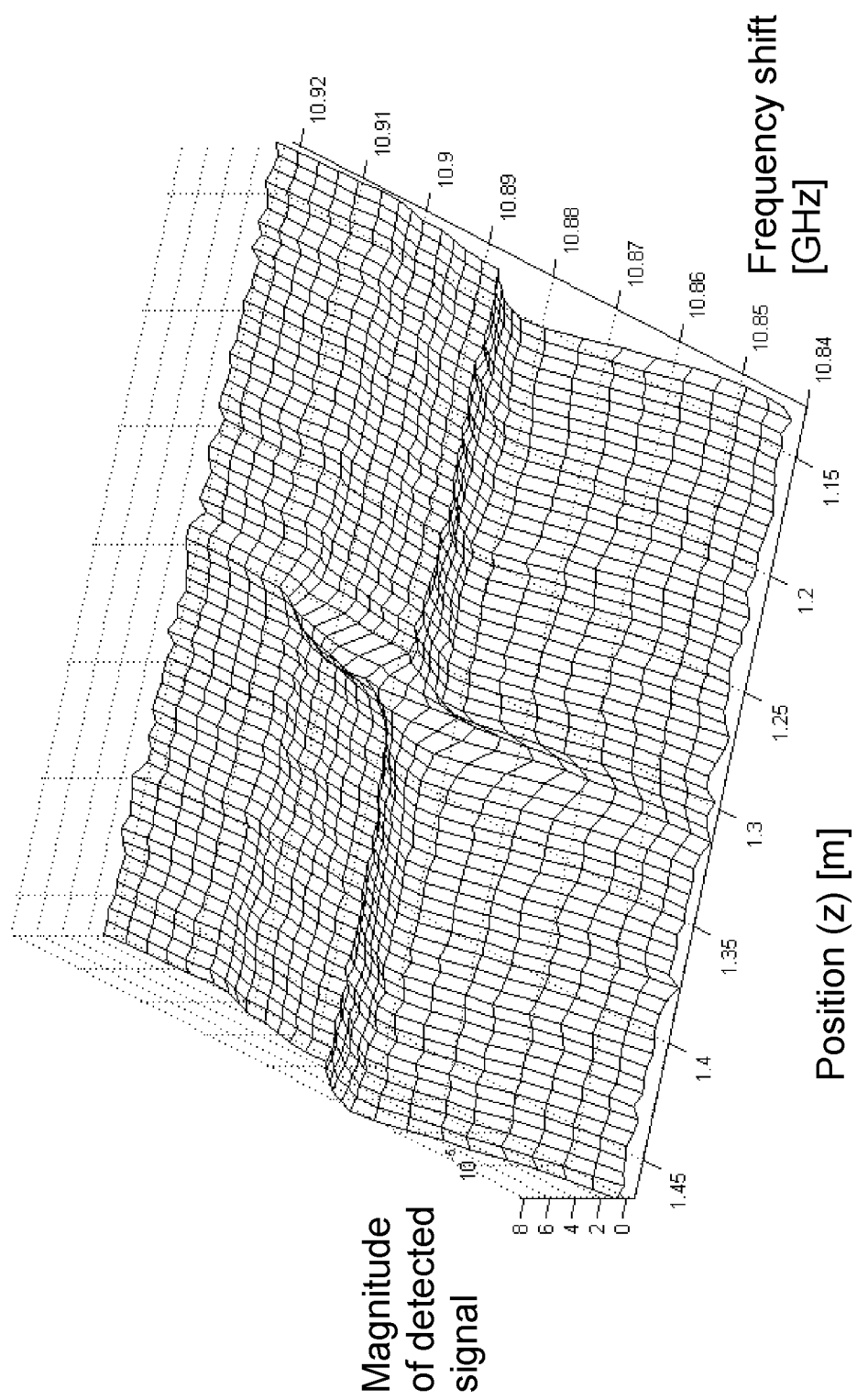
FIG. 4 schematically depicts an exemplary measurement result using the system of FIG. 2, in a form of a map, in accordance with some embodiments of the disclosure.

Experimental test results may be displayed in a form of a map. A first axis of such a map may be the distance along the deployed optical fiber (denoted for example by meters on a z axis). A second axis may be a local Brillouin frequency shift. FIG. 4 schematically depicts an exemplary measurement result using the system of FIG. 2, in a form of a map. In FIG. 4, the magnitude of detected light signals is presented as a function of the distance along the fiber and as a function of a frequency shift. High magnitudes of detected signals, compared to the background, are observed around a frequency shift of 10.88 GHz along the entire z axis representing the distance along the fiber, from 1.14 m to 1.45 m, except at about 1.3 m, where high magnitude is observed at a Brillouin frequency shift of about 10.9 GHz, indicating a local variance of the optical fiber around the 1.3 m position.

It will be appreciated that, generally, a measurement signal is obtained from a portion or portions of the optical fiber wherein SBS occurs; that is to say a portion or portions of the optical fiber where a correlation peak is present. Further, measurement noise is generally related to portions of the optical fiber wherein SBS does not occur. By modulating the pump light wave, or the probe light wave, or both, by pulse modulation, measurement noise may be considerably be reduced. In some embodiments, by synchronizing the timing of the pulses with a pseudo-random bit sequence, measurement noise may be considerably reduced compared to the signal, thereby signal to noise ratio may be increased.

Figure 5:
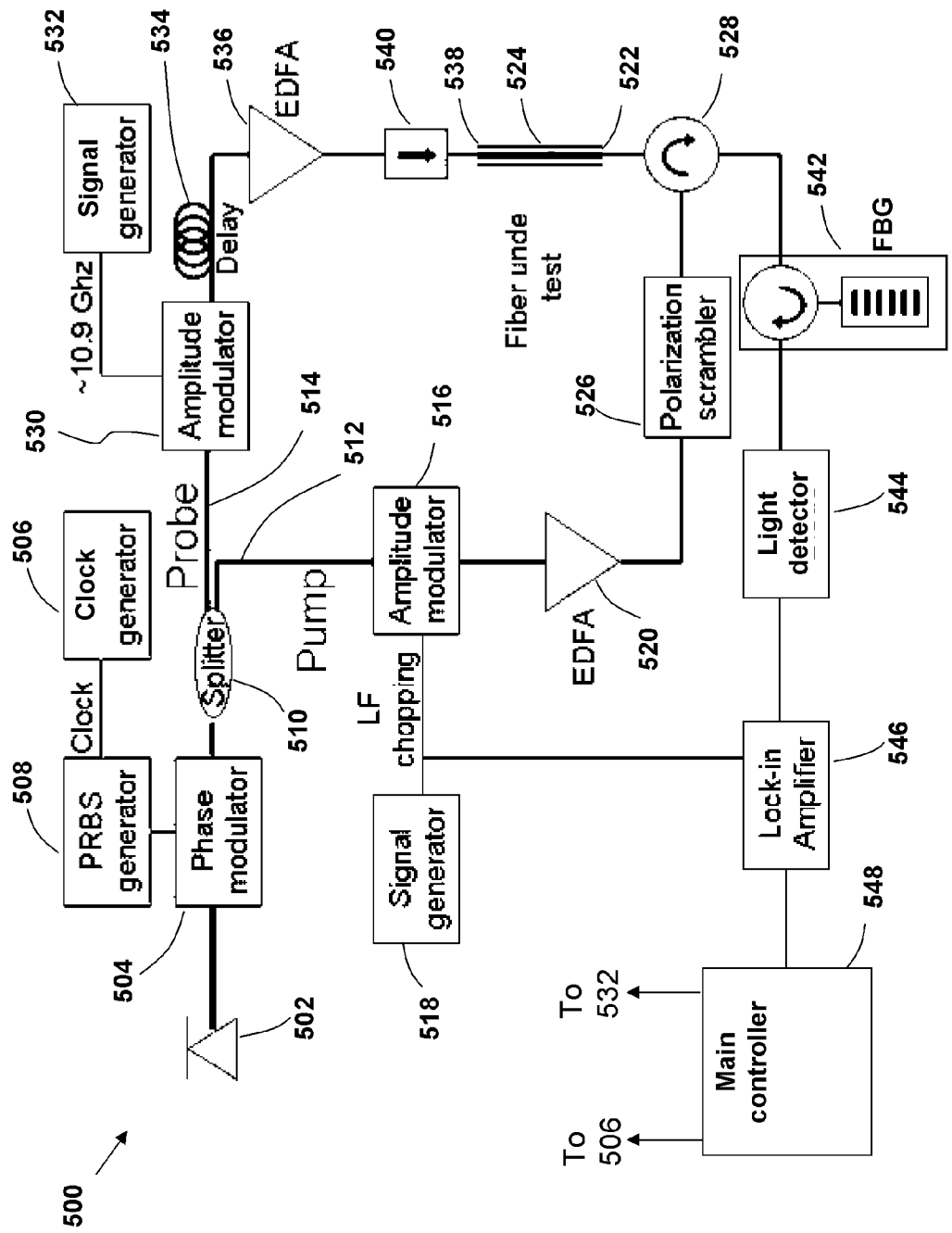
FIG. 5 schematically depicts a system configured to carry out distributed sensing using an optical fiber in accordance with some embodiments of the disclosure.

FIG. 5 schematically depicts an embodiment of a system 500 for distributed sensing of one or more measurable parameters of an optical fiber or a monitored object interfaced with an optical fiber, according to an aspect of the invention. In system 500 a single Pseudo-random signal is used to phase-modulate a pump light wave that propagates in an optical fiber in one direction, and a probe light wave, that propagates in the optical fiber in the opposite direction. The pseudo-random signal comprises repeating pseudo-random bit sequences, each having a length M and a bit duration T, and therefore a sequence time duration of M·T. A correlation peak of a high order ($7^{th}$ order in this example) is employed for interrogating the local Brillouin frequency shift, by delaying one of the two phase-modulated light waves, e.g., the probe light wave, by a time delay $\Delta T$ relative to the other light wave. The time delay $\Delta T$ is constant and approximately equal to the desired order of the correlation peak N multiplied by the time duration of the sequence: $\Delta T=NMT$ (N=7 in this example). The pseudo-random bit sequence repeats every M bits, that is to say, portions of the pseudo-random signal that are M bits apart, are identical. Consequently, delaying one of the two phase-modulated waves by a time delay that is a multiple of the time duration of the sequence, generates a correlation peak in the optical fiber between two sequences of the pseudo-random signal that are generated with a time gap $\Delta T$ therebetween. When the correlation peak is obtained using portions of the pseudo-random signal that are substantially identical but are generated with a time gap $\Delta T$ between them as described above, scanning the position of the correlation peak along the optical fiber is done, in some embodiments, by suitably varying the time duration of the pseudo-random bit sequence MT. In some embodiments, scanning the position of the correlation peak is done by suitably varying the bit time duration T. In some embodiments scanning the position of the correlation peak is done by suitably varying the pseudo-random bit sequence length M.

System 500 comprises a light source 502, such as a distributed feedback (DFB) laser diode, configured to generate a coherent light wave at a frequency $\omega_0$. Light source 502 is functionally associated with a phase modulator 504. Phase modulator 504 is configured to phase-modulate the light wave generated by light source 502, thereby generating a light wave having a frequency centered at $\omega_0$. A clock generator 506, such as a microwave generator is functionally associated with a PRBS generator 508, for providing PRBS generator 508 a clock signal. PRBS generator 508 is functionally associated with phase modulator 504, for providing a modulation signal to phase-modulate the light wave generated by light source 502. PRBS generator 508 is configured to generate a pseudo-random bit sequence with equal probabilities of "0"s and "1"s at a rate greater than 1 GHz and smaller than 100 GHz. The rate of the pseudo-random bit signal generated by PRBS generator 508 is determined by the frequency of the clock signal of clock generator 506. Clock generator 506 is tunable, allowing to controllably change the frequency of the clock signal, and consequently to controllably change the rate of the generated pseudo-random signal. A desired clock rate may be selected so as to obtain a desired width of a correlation peak, and a desired pseudo-random bit sequence length M may be selected so as to allow an unambiguous interrogation of a desired length of an optical fiber. For example, at a clock rate of about 8 GHz (generating a pseudo random signal of the same rate) a single bit time duration T is about 60 pico-sec, corresponding to a correlation peak width $\Delta z$ of about 1.2 cm in the optical fiber. For example, a pseudo-random bit sequence length $M=2^{15}-1$ allows an unambiguous measurement of an optical fiber length of about $M \cdot \Delta z \cong 400$ m. For example, a pseudo-random bit sequence length of about $2^{22}$ allows an unambiguous measurement of an optical fiber length of about 50 km with the same spatial resolution of 1.2 cm. By selecting a suitable sequence length, lower than about $2^{15}$, or higher than about $2^{15}$, a desired spatial range of measurement (length of optical fiber) is achieved.

It is noted that employing an anharmonic modulation signal, such as a pseudo-random signal, for modulating e.g. the phase of the pump light wave, allows independently selecting the width of the correlation peak and the spatial range of unambiguous measurement: The width of the correlation peak is determined by the rate of the pseudo-random bit sequence signal and the corresponding bit time duration, whereas the spatial range of measurement is determined by the length M of the pseudo-random bit sequence. This is opposed to the intrinsic dependency between the width of the correlation peak and the spatial range of unambiguous measurement in known methods that employ a substantially harmonic signal, or a combination of a limited number of harmonic signals, to modulate the pump light wave. Thus, by employing an anharmonic modulation signal, the disclosed method allows for removing the limiting trade off of known methods, between spatial resolution and spatial range of measurement.

A splitter 510 is functionally associated with phase modulator 504, for splitting the phase-modulated light wave to a pump light wave in pump branch 512 and a probe light wave in probe branch 514. Low frequency amplitude modulator 516 on pump brunch 512 is functionally associated with splitter 510 and with a low frequency signal generator 518. Low frequency amplitude modulator 516 is configured for amplitude-modulating the pump light wave with a low frequency modulation signal from low frequency signal generator 518, to enhance signal to noise ratio, as is explained further below. A pump erbium-doped fiber (EDF) amplifier 520 is functionally associated with low frequency amplitude modulator 516, and with a first end 522 of an optical fiber 524, through a polarization scrambler 526 and through a circulator 528. Pump EDF amplifier 520 is thereby configured for amplifying the pump light wave and for transmitting the amplified pump light wave into optical fiber 524 through first end 522.

Polarization scrambler 526 is functionally associated with pump EDF amplifier 520 and with circulator 528. Polarization scrambler 526 is configured to avoid polarization-related fading of the amplified pump light wave.

An amplitude modulator 530 on probe branch 514 is functionally associated with splitter 510, and configured to amplitude-modulate the probe light wave at a frequency $\Omega$, to obtain two side bands at $\omega_0-\Omega$ and $\omega_0+\Omega$. A modulation signal generator 532 is functionally associated with amplitude modulator 530 and configured for supplying amplitude modulator 530 a tunable modulation signal at a frequency of about 10.9 GHz, approximately equal to the Brillouin frequency shift $\Omega_B$. Amplitude modulator 530 is further biased to suppress the fundamental frequency component $\omega_0$, thus generating a phase-modulated probe light wave having spectral components at $\omega_0-\Omega$ and $\omega_0+\Omega$. The spectral component at $\omega_0+\Omega$ is blocked as is explained below, and the spectral component at $\omega_0-\Omega$ is employed as a probe light wave having a frequency centered at $\omega_1$, shifted from $\omega_0$ by a frequency gap $\Omega$.

A delay imbalance 534 is functionally associated with amplitude modulator 530. Delay imbalance 534 is configured for delaying the probe light wave by a time duration $\Delta T$ equal to a selected integer N multiplied by the time duration of a single pseudo-random bit sequence, such that $\Delta T=NMT$. For example, a correlation peak of a seventh-order between the probe light wave and the pump light wave, may be generated within optical fiber 524 by selecting N=7 and a corresponding time delay $\Delta T$. A probe EDF amplifier 536 is functionally associated with delay imbalance 534, and with a second end 538 of optical fiber 524, through an isolator 540. Probe EDF amplifier 536 is configured for amplifying the probe light wave and consequently for transmitting the probe light wave into optical fiber 524 through second end 538. Isolator 540 is configured to block light waves that may be emitted from second end 538 to probe EDF amplifier 536.

First end 522 is functionally associated with a light signal detector 544, such as a photo diode, through circulator 528 and through fiber-Bragg grating 542. Fiber-Bragg grating 542 is functionally associated with circulator 528 and with light signal detector 544, and is configured to block spectral components of the probe light wave having frequencies equal or greater than $\omega_0+\Omega$, allowing the lower spectral component at $\omega_0-\Omega$ into light signal detector 544. Light signal detector 544 is functionally associated with a lock-in amplifier 546 and is configured for detecting light signals emitted from first end 522 of optical fiber 524, through circulator 528 and through fiber-Brag grating 542.

Lock-in amplifier 546 is functionally associated with low frequency signal generator 518. Lock-in amplifier 546 is configured to amplify detected light signals from light signal detector 544 at the low frequency generated by low frequency signal generator 518 that modulates the pump light wave through low frequency amplitude modulator 516, thereby suppressing spurious signals resulting from spontaneous Brillouin scattering at the probe light wave frequency.

Main controller 548 is functionally associated with lock-in amplifier 546 to receive amplified signals therefrom. Main controller 548 is further functionally associated with clock generator 506, for controlling the clock rate of PRBS generator 508. Main controller 548 is further functionally associated with modulation signal generator 532 for controlling the frequency difference $\Omega$ between the pump light wave frequency and the probe light wave frequency.

In operation, the probe light wave is amplified inside optical fiber 524, at the position of the correlation peak, if the probe light wave frequency and the pump light wave frequency differ by exactly $\Omega_B$, namely the local Brillouin frequency shift, substantially as explained with reference to FIG. 3 above. Amplified probe light wave signals are emitted from first end 522 of optical fiber 524, detected by light signal detector 544 and amplified by lock-in amplifier 546.

Sensing of a measurable parameter using optical fiber 524 is carried out for example as follows. Main controller 548 controls clock generator 506 to vary the clock rate of PRBS generator 508, thereby affecting a change in location of the correlation peak along optical fiber 524. By suitably varying the clock rate of clock generator 506, the correlation peak is made to scan a desired portion of optical fiber 524, for example the entire length of optical fiber 524. Substantially at every location of the correlation peak inside optical fiber 524, main controller 548 controls modulation signal generator 532 to vary the frequency of the modulation signal modulating the probe light wave, thereby varying the frequency difference Ω. The difference Ω between the pump light wave frequency and the probe light wave frequency is scanned over a frequency range that includes the nominal Brillouin frequency shift $Ω_B$ of optical fiber 524 in normal conditions, and includes variances of the Brillouin frequency shift, due to expected variances from normal conditions in a sensed measurable parameter, such as strain and temperature. Measurement results are presented for example substantially as explained with reference to FIG. 4 above, by displaying the magnitude of light signals detected by light signal detector 544 on a map having one axis denoting the distance along optical fiber 524 and a second axis denoting a frequency shift.

Random Phase Modulation, Polarization Maintaining Optical Fibers

Figure 6:
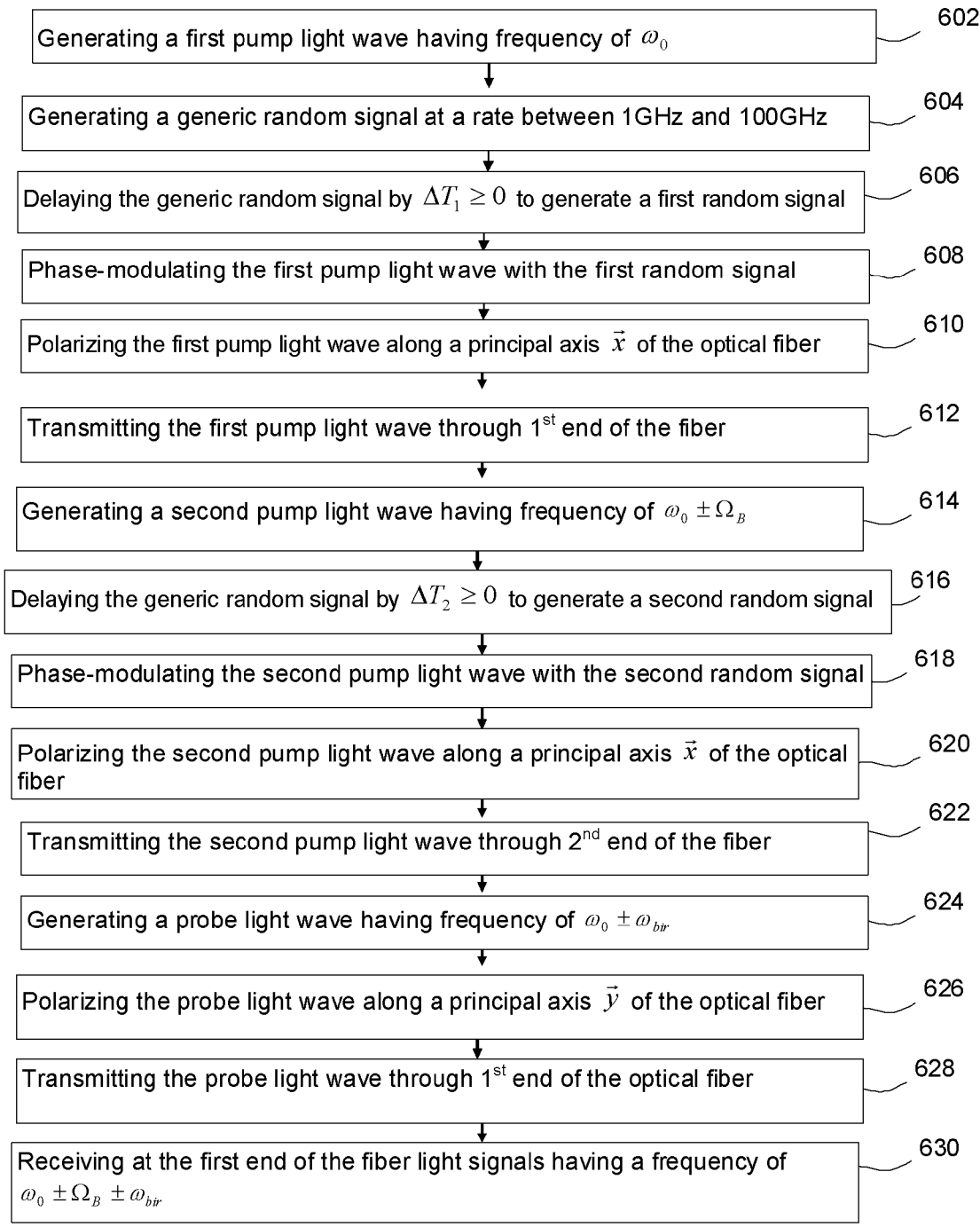
FIG. 6 schematically illustrates a method for distributed sensing using a polarization maintaining optical fiber, in accordance with some embodiments of the disclosure.

Reference is now made to FIG. 6, showing an exemplary embodiment of a method for distributed sensing of one or more measurable parameters of a polarization maintaining (PM) optical fiber:

The method may comprise step 602 of generating a first light wave having a frequency centered at $ω_0$.

The method may further comprise step 604 of generating a generic random signal having a frequency centered substantially between 1 GHz and 100 GHz, The method may further comprise step 606 of generating a first random signal by delaying the generic pseudo-random signal by a time delay $ΔT_1 ≥ 0$.

The method may further comprise step 608 of modulating the phase of the first light wave by the first random signal, thereby generating a first modulated light wave.

The method may further comprise step 610 of polarizing the first light wave along a first principal axis $\vec{x}$ of the polarization maintaining optical fiber, thereby generating a first modulated pump light wave.

The method may further comprise step 612 of transmitting the first modulated pump light wave into the optical fiber through a first end thereof;

The method may further comprise step 614 of generating a second light wave having a frequency of $ω_1$, shifted from $ω_0$ by approximately $Ω_B$, $Ω_B$ being a Brillouin frequency shift of the optical fiber.

The method may further comprise step 616 of generating a second random signal by delaying the generic random signal by a time delay $ΔT_2 ≥ 0$.

The method may further comprise a step 618 of modulating the phase of the second light wave by the second random signal, thereby generating a second modulated light wave.

The method may further comprise step 620 of polarizing the second modulated light wave along the polarization direction of the first pump light wave $\vec{x}$, thereby generating a second modulated pump light wave.

The method may further comprise step 622 of transmitting the second modulated pump light wave into the optical fiber through a second end thereof.

The method may further comprise step 624 of generating a probe light wave having a frequency of $ω_2$, shifted from $ω_0$ by approximately $ω_{bir}$, $ω_{bir}$ being a birefringence frequency difference in the optical fiber.

The method may further comprise step 626 of polarizing the probe light wave along a second principal axis $\vec{y}$ of the polarization maintaining optical fiber.

The method may further comprise step 628 of transmitting the probe light wave into the optical fiber through the first end thereof.

The method may further comprise step 630 of receiving at the first end of the optical fiber light wave signals, having a frequency approximately equal to $ω_{sig}$, wherein $ω_{sig}$ is shifted from the frequency $ω_2$ of the probe signal by approximately $Ω_B$, $Ω_B$ being a Brillouin frequency shift of the optical fiber.

The first pump light wave and the second pump light wave, both polarized along a principal axis $\vec{x}$ of the PM optical fiber, generate together by SBS an acoustic wave in the polarization maintaining optical fiber, if the frequencies of the two light waves differ by exactly the Brillouin frequency shift $Ω_B$. A probe light wave is polarized along a second principal axis $\vec{y}$ of the PM optical fiber and transmitted into the optical fiber from the first end thereof. The probe light wave is effectively backscattered by the generated acoustic wave, if the wavelength of the probe wave is equal to that of one of the pump waves. The propagation indices, $n_x$ and $n_y$, along the principal axes x and y of the polarization maintaining (PM) optical fiber are different. Therefore, is the wave length of the probe wave is equal to that of one of the pump waves, the frequency of the probe light wave, ω2, is generally different from the frequencies of any of the pump waves. A frequency difference between two light waves, polarized along the $\vec{x}$ and $\vec{y}$ principal axes of an optical fiber, respectively, and having the same wavelength, is referred herein as "birefringence frequency difference". The birefringence frequency difference between two light waves as described above is approximately $$ω_{bir} ≈ \frac{Δn}{n}ω,$$

where n is the average of the propagation indices $n_x$ and $n_y$, Δn is the difference between them, and w is the average frequency of the waves. In the expression for $ω_{bir}$ above, Δn is always taken as an absolute value of the difference between $n_x$ and $n_y$, hence $ω_{bir}$ is always positive. It will be appreciated that for a standard optical fiber in which $n_x = n_y$, $ω_{bir} = 0$.

Backscattering of the probe wave by the acoustic wave in the PM optical fiber, generates a signal light wave, propagating in the opposite direction to that of the probe wave, and having a frequency shifted from that of the probe wave by the Brillouin frequency shift, $Ω_B$. Thus, according to the method, employing a PM optical fiber, having substantially at least two optical axes, allows in some embodiments and compared with methods employing standard optical fibers, for better separation in the frequency domain between a transmitted pump light wave, and light wave signals received and detected for sensing. Such better separation allows for enhancing the signal to noise ratio of the measurement and consequently enhancing measurement sensitivity and accuracy. Furthermore, the signal light wave has a polarization that is orthogonal to the polarization of the pump light waves, and therefore could be detected with little interference from the pump light waves or without any such interference at all.

Figure 7A:
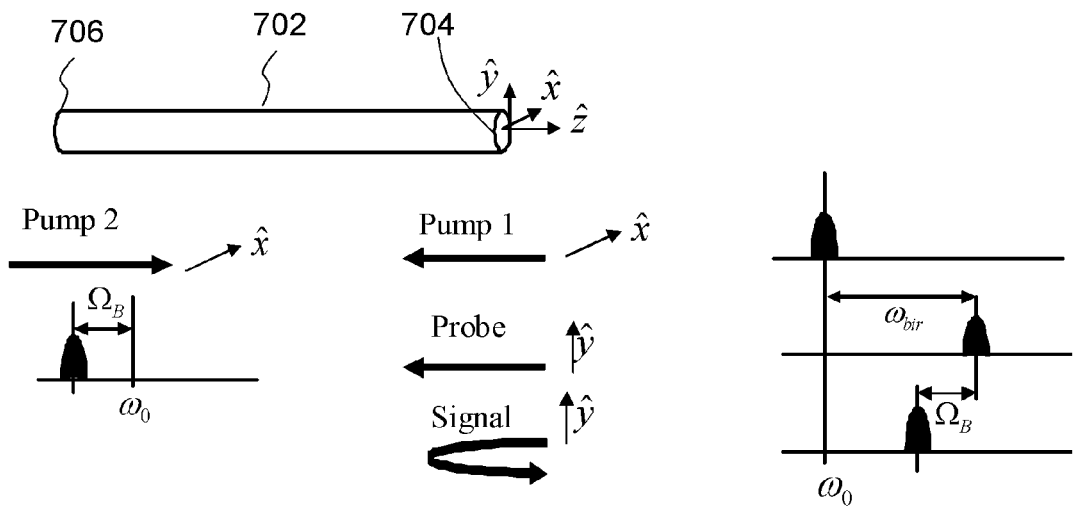
FIGS. 7A to 7D schematically illustrate the frequencies, polarization directions and propagation directions of light waves in a polarization maintaining optical fiber, in accordance with some embodiments of the disclosure.

FIGS. 7A-7D illustrate schematically the frequencies, polarization directions and propagation directions in a PM optical fiber, of the light waves involved in four exemplary embodiments, respectively, as described herein. In FIG. 7A a PM optical fiber 702 has two orthogonal principal axes, x̂ and ŷ, associated with two different propagation indices, $n_x$ and $n_y$, respectively. A first pump light wave, having a frequency of $ω_0$ and a polarization along the x̂ direction, is transmitted through a first end 704 into PM optical fiber 702, thereby propagating along the negative ẑ direction. A second pump light wave, having a frequency of $ω_0 - Ω_B$ and a polarization along the $\hat{x}$ direction, is transmitted through a second end 706 into PM optical fiber 702, thereby propagating along the positive $\hat{z}$ direction.

A probe light wave, having a frequency of $\omega_0+\omega_{bir}$ and a polarization along the $\hat{y}$ direction, is transmitted through first end 704, and propagates along the negative $\hat{z}$ direction. A signal light wave is generated by backscattering of the probe light wave within PM optical fiber 702 through SBS. The signal light wave is thereby propagating in the positive $\hat{z}$ direction, having polarization along the $\hat{y}$ direction and a frequency of $\omega_0+\omega_{bir}-\Omega_B$.

Figure 7B:
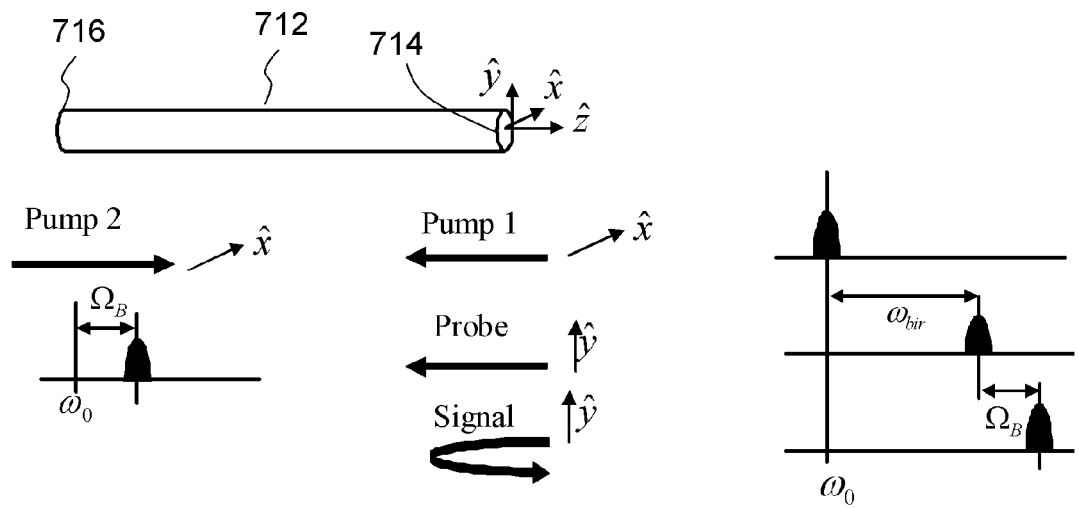

In some embodiments depicted schematically in FIG. 7B, a first pump light wave, having a polarization along the $\hat{x}$ direction and a frequency of $\omega_0$, is transmitted through a first end 714 into a PM optical fiber 712 thereby propagating along the negative $\hat{z}$ direction. A second pump light wave, having a frequency of $\omega_0+\Omega_B$ and a polarization along the $\hat{x}$ direction, is transmitted through a second end 716, thereby propagating along the positive $\hat{z}$ direction. A probe light wave, having a frequency of $\omega_0+\omega_b$, and a polarization along the $\hat{y}$ direction, is transmitted through first end 714, and propagates along the negative $\hat{z}$ direction. A reflected signal light wave, generated by backscattering of the probe light wave, propagates in the positive $\hat{z}$ direction, having a polarization along the $\hat{y}$ direction and a frequency of $\omega_0+\omega_{bir}+\Omega_B$.

Figure 7C:
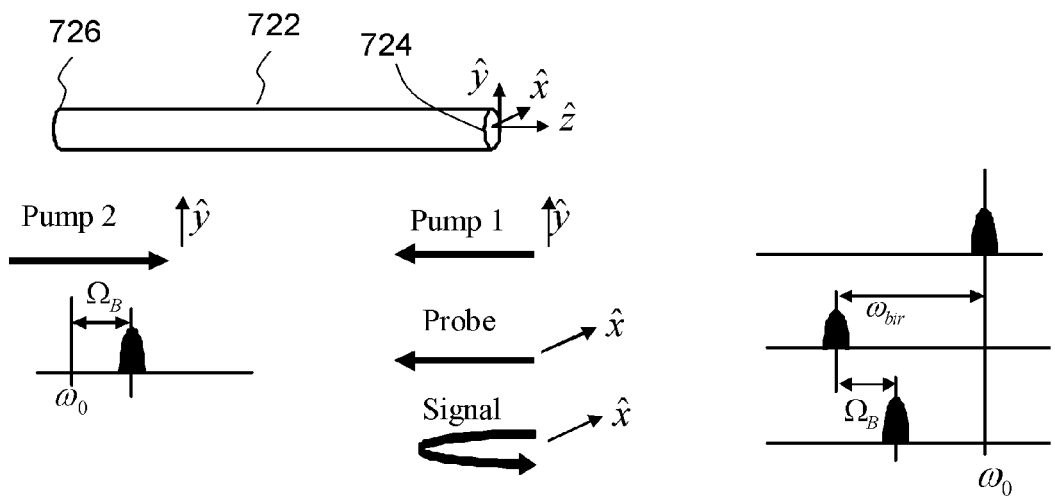

In some embodiments depicted schematically in FIG. 7C a first pump light wave, polarized along the $\hat{y}$ direction and having a frequency of $\omega_0$, is transmitted through a first end 724 into a PM optical fiber 722 and propagates along the negative $\hat{z}$ direction. A second pump light wave, having a frequency of $\omega_0+\Omega_B$ and a polarization along the $\hat{y}$ direction, is transmitted through a second end 726, thereby propagating along the positive $\hat{z}$ direction. A probe light wave, having a frequency of $\omega_0-\omega_b$, and a polarization along the $\hat{x}$ direction, is transmitted through first end 724, and propagates along the negative $\hat{z}$ direction. A reflected signal light wave, generated by backscattering of the probe light wave, propagates in the positive $\hat{z}$ direction, having a polarization along the $\hat{x}$ direction and a frequency of $\omega_0-\omega_{bir}+\Omega_B$.

Figure 7D:
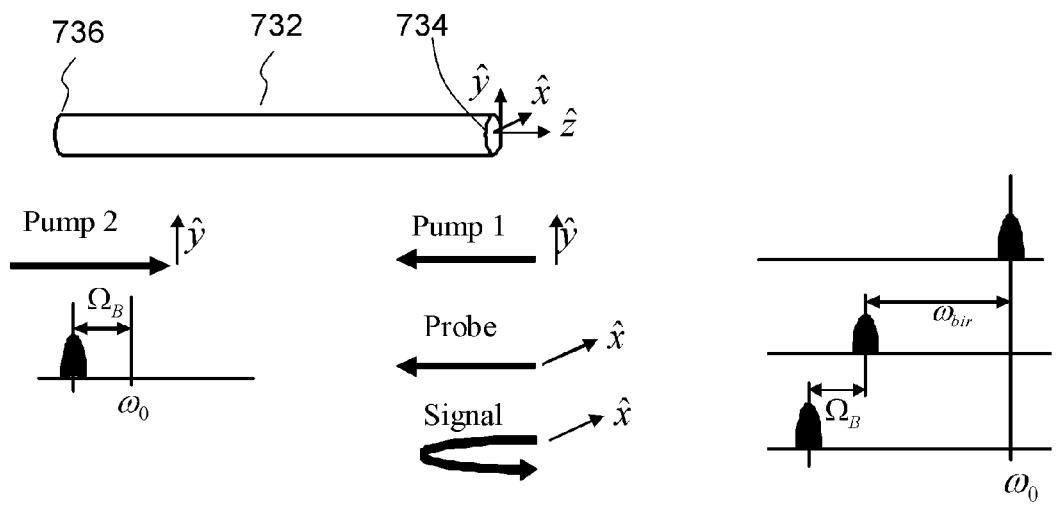

In some embodiments depicted schematically in FIG. 7D a first pump light wave, having a polarization along the $\hat{y}$ direction and a frequency of $\omega_0$, is transmitted through a first end 734 into a PM optical fiber 732 and propagates along the negative $\hat{z}$ direction. A second pump light wave, having a frequency of $\omega_0-\Omega_B$ and polarization along the $\hat{y}$ direction, is transmitted through a second end 736, thereby propagating along the positive $\hat{z}$ direction. A probe light wave, having a frequency of $\omega_0-\omega_{bir}$ and a polarization along the $\hat{x}$ direction, is transmitted through first end 734, and propagates along the negative $\hat{z}$ direction. A reflected signal light wave, generated by backscattering of the probe light wave, propagates in the positive $\hat{z}$ direction, having polarization along the $\hat{x}$ direction and a frequency of $\omega_0-\omega_{bir}-\Omega_B$.

In some embodiments employing a PM optical fiber for distributed sensing according to the teachings herein is advantageous over employing a standard optical fiber, because typically $\omega_{bir}$ is greater than $\Omega_B$. The difference between propagation indices $n_x$ and $n_y$, is typically and approximately $5 \cdot 10^{-4}$, corresponding to a birefringence frequency difference $\omega_{bir}$ of about $2\pi \cdot 80$ GHz. A greater frequency separation between the frequencies of the two pump light waves and the frequency of the detected signal light wave, allows for enhancement of signal to noise ratio in the measurement and consequently enhances measurement accuracy and repeatability.

In some embodiments employing a PM optical fiber for distributed sensing according to the teachings herein is further advantageous over employing a standard optical fiber, because the birefringence frequency difference $\omega_{bir}$ itself depends on temperature and strain. Thus, in case strain, for example, is applied to a PM optical fiber, such strain may be detected by monitoring $\omega_{bir}$, independently from monitoring $\Omega_B$. Two such mutually independent measurements of a same measurable parameter may enable direct comparison or combination between the two, thereby enhancing measurement reliability and accuracy. Moreover, Brillouin frequency shift $\Omega_B$ and birefringence frequency difference $\omega_{bir}$ may change differently in response to a temperature variance. That is to say: $\Omega_B$ increases in response to both temperature increase and strain increase. Birefringence frequency difference $\omega_{bir}$ increases in response to strain increase, but decreases in response to temperature increase. Thus, by independently monitoring the variance of $\Omega_B$ and $\omega_{bir}$ during distributed sensing according to the teachings herein, it is possible to distinguish between temperature variance and strain variance as the source for such measurement results.

PM optical fibers are typically much more expensive than standard fibers, and are therefore generally used over shorter distances. Typical length of PM optical fibers that are used for distributed sensing according to known methods is on the order of hundreds of meters, compared to lengths of tens of kilometers of deployed standard optical fibers. A method for enhancing spatial resolution, according to the teachings herein, is therefore particularly important when employed with a PM optical fiber.

Figure 8:
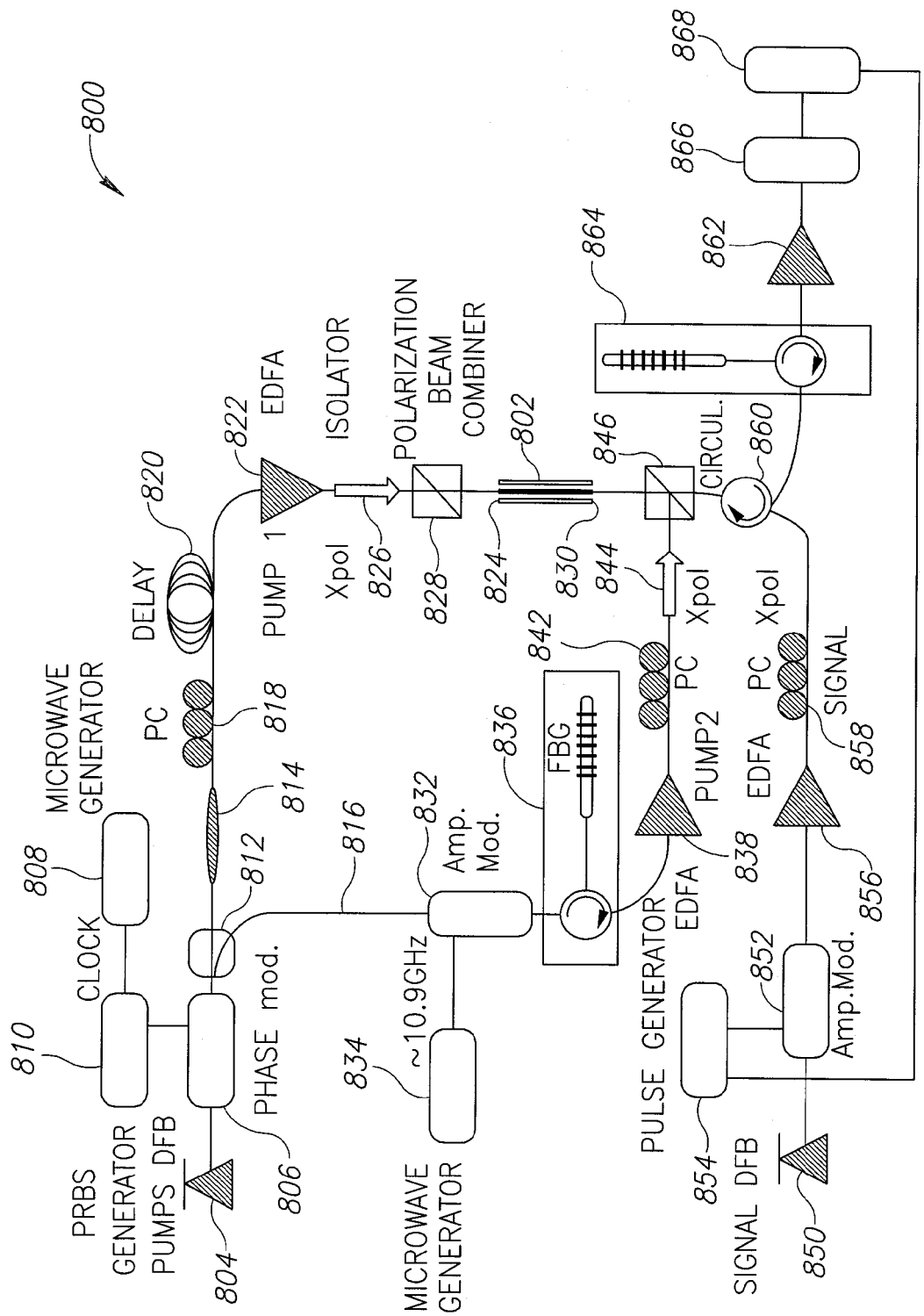
FIG. 8 schematically depicts a system configured to carry out distributed sensing using a polarization maintaining optical fiber in accordance with some embodiments of the disclosure.

Reference is now made to FIG. 8, depicting schematically an embodiment of a system 800, comprising a PM optical fiber 802, as is explained below. PM optical fiber 802 has at least two distinct principal axes, denoted $\hat{x}$ and $\hat{y}$, characterized by different propagation indices $n_x$ and $n_y$.

System 800 further comprises a pump light source 804 functionally associated with a phase modulator 806. Pump light source 804 may be a distributed feedback (DFB) laser diode, generating a coherent light wave at a frequency $\omega 0$. Phase modulator 806 is configured to phase-modulate the light wave generated by pump light source 804. A clock generator 808 is functionally associated with a PRBS generator 810, for providing PRBS generator 810 a clock signal at a nominal clock rate greater than about 1 GHz and smaller than about 100 GHz. PRBS generator generates a pseudo-random bit sequence, substantially as is explained above regarding PRBS generator 508 in FIG. 5. Further, the clock rate of the clock signal of clock generator 808 determines the bit time duration T of the pseudo-random bit sequence as is explained herein. Clock generator 808 is tunable, allowing externally-controlled variation of the clock rate, thereby varying the time duration T. PRBS generator 810 is functionally associated with phase modulator 806, for providing a modulation signal to phase-modulate the light wave generated by pump light source 804. PRBS generator 810 generates a binary pseudo-random bit sequence with equal probabilities of "0"s and "1"s. At a clock rate of about 2 GHz for example, a single bit time duration T=500 pSec corresponds to a correlation peak width $\Delta z$ of about 5 cm in PM optical fiber 802.

A splitter 812 is functionally associated with phase modulator 806, for splitting the phase-modulated light wave to a first pump light wave in first pump branch 814 and a second pump light wave in second pump branch 816. A first polarization controller 818 on first pump brunch 814 is functionally associated with splitter 812. First polarization controller 818 is configured to polarize the first pump light wave along the $\hat{x}$ polarization direction of PM optical fiber 802.

A delay imbalance 820 is functionally associated with first polarization controller 818. Delay imbalance 820 is configured for delaying the first pump light wave, affecting thereby a correlation peak of high order between the first pump light wave and the second pump light wave, substantially as is explained with reference to FIG. 5 above.

A first pump EDF amplifier 822 is functionally associated with delay imbalance 820, and with a first end 824 of PM optical fiber 802, through a first isolator 826 and a first polarization beam combiner 828. First pump EDF amplifier 822 is configured for amplifying the first pump light wave and consequently for transmitting the first pump light wave into PM optical fiber 802 through first end 824, at a power of about 200 mW.

First polarization beam combiner 828 is functionally associated with first isolator 826 and with first end 824 of PM optical fiber 802. First polarization beam combiner 828 is configured for maintaining suitable separation between light waves having orthogonal polarization that pass therethrough. Particularly, first polarization beam combiner 828 is configured to maintain the polarization of the first pump light wave transmitted into PM optical fiber 802, and maintain suitable separation of the first pump light wave from light wave signals polarized along the $\hat{y}$ direction, that are emitted in some instances from first end 824.

On second pump branch 816, a pump amplitude modulator 832 is functionally associated with splitter 812, and configured to amplitude-modulate the second pump light wave at a frequency $\Omega$, to obtain two side bands at $\omega_0 - \Omega$ and $\omega_0 + \Omega$. A modulation signal generator 834 is functionally associated with pump amplitude modulator 832 and configured for supplying pump amplitude modulator 832 a tunable modulation signal at a frequency $\Omega$ of about 10.9 GHz. Pump amplitude modulator 832 is further biased to suppress the fundamental frequency component $\omega_0$, thus generating a phase-modulated pump light wave having spectral components at $\omega_0 - \Omega$ and $\omega_0 + \Omega$. A fiber-Bragg grating 836, functionally associated with pump amplitude modulator 832 is configured for filtering out the lower side band at $\omega_0 - \Omega$, thereby generating a second pump light wave at a frequency $\omega_0 + \Omega$.

A second pump EDF amplifier 838 is functionally associated with pump amplitude modulator 832 through fiber-Bragg grating 836. Second pump EDF amplifier 838 is further functionally associated with a second end 830 of PM optical fiber 802, through a second polarization controller 842, through second isolator 844 and through second polarization beam combiner 846. Second pump EDF amplifier 838 is configured for amplifying the second pump light wave and for transmitting the amplified second pump light wave into PM optical fiber 802 through second end 830 at a power of about 200 mW.

Second polarization controller 842 is configured to polarize the second pump light wave along the polarization direction of the first pump light wave, namely along the $\hat{x}$ polarization direction of PM optical fiber 802.

Second polarization beam combiner 846 is functionally associated with second isolator 844, with circulator 860 and with second end 830 of PM optical fiber 802. Second polarization beam combiner 846 is configured for maintaining suitable separation between light waves having orthogonal polarization that pass therethrough. Particularly, second polarization beam combiner 846 is configured to maintain the $\hat{x}$ polarization of the second pump light wave transmitted into PM optical fiber 802, and maintain the $\hat{y}$ polarization of the probe light wave from circulator 860 (further detailed below) as the two waves combine at second end 830 of PM optical fiber 802. Furthermore, second polarization beam combiner 846 enables only light waves having a $\hat{y}$ polarization from second end 830 to circulator 860, thereby blocking undesired light waves associated with the first pump light wave and the second pump light wave, that are polarized along the $\hat{x}$ direction.

System 800 further comprises a probe light source 850. Probe light source 850 may comprise a distributed feedback (DFB) laser diode, generating a coherent light wave at a tunable frequency $\omega_2$, approximately equal to $\omega_0 + \omega_{bir} \cdot \omega_2$ may be varied for example by varying an operational temperature of the DFB laser diode or a current supplied thereto. A Probe amplitude modulator 852, functionally associated with probe light source 850 and with a low frequency pulse generator 854, is configured to pulse-modulate the probe light wave, to allow enhancing the signal to noise ratio of the detected signal, as is explained further below. Low frequency pulse generator 854 may generate for example a 60 KHz pulse signal for modulating the probe light wave.

A probe EDF amplifier 856 is functionally associated with probe amplitude modulator 852. Probe EDF amplifier 856 is configured to amplify the probe light wave and to transmit the probe light wave to PM optical fiber 802 through a probe polarization controller 858, through a circulator 860, through second polarization beam combiner 846 and through second end 830 of PM optical fiber 802. Probe polarization controller 858 is functionally associated with probe EDF amplifier 856, and is configured to polarize the probe light wave along a principal axis $\hat{y}$ of the PM optical fiber.

Signal EDF amplifier 862 is functionally associated with second end 830 of PM optical fiber 802 through second polarization beam combiner 846, through circulator 860 and through signal fiber Bragg grating 864. Signal EDF amplifier 862 is configured to amplify light signals that are emitted from second end 830 of PM optical fiber 802. Signal fiber-Bragg grating 864, functionally associated with circulator 860 is configured for filtering out light signals having spectral components around the frequencies of the first pump light wave and the second pump light wave, thereby reducing measurement noise considerably.

A signal detector 866 is functionally associated with signal EDF amplifier 862 and configured for detection of light signals amplified by signal EDF amplifier 862. A lock-in amplifier 868, is functionally associated with signal detector 866 and with low frequency pulse generator 854. Lock in amplifier 868 is configured to amplify detected signals from signal detector 866, which coincide in frequency and phase, to the low frequency (60 KHz) signal generated by low frequency pulse generator 854, thereby enhancing further signal to noise ratio of the measurement.

In operation the bit time duration T in the pseudo-random bit sequence generated by PRBS generator 810, is varied to affect a correlation peak between the first pump light wave and the second pump light wave, and thus to scan at least a portion of the length of PM optical fiber 802, substantially as described above with reference to FIG. 8. Further, modulation signal generator 834 is controlled to vary the frequency $\Omega$ of the modulation signal to pump amplitude modulator 832, thereby varying the frequency difference $\Omega$ between the frequencies of the first pump light wave and the second pump light wave. Furthermore, the frequency of the probe light wave, generated by probe light source 850, is controllably varied, thereby varying the frequency difference between the frequencies of the second pump light wave and the probe light wave.

In some embodiments, a measurement using a system such as schematically illustrated in FIG. 8, obtains a magnitude of detected light wave signals as a function of position of a correlation peak of the first pump light wave and the second pump light wave along PM optical fiber 802; as a function of a frequency shift $\Omega$ between the frequencies of the first pump light wave and the second pump light wave; or as a function of a frequency shift $\Delta\omega$ between the frequencies of the probe light wave and the corresponding pump light wave (corresponding pump light wave relates to pump light wave that propagates in the same direction as the probe light wave in the optical fiber). Sustainable acoustic wave as described above, and resulting SBS, occur at a position of the correlation peak along the optical fiber, if the frequency shift $\Omega$ is equal to the local Brillouin frequency shift of the optical fiber at the location of the correlation peak. Further, effective reflection of the probe light wave by the generated acoustic wave occurs if the frequency difference $\Delta\omega$ between the frequencies of the probe light wave and the corresponding pump light wave is equal to the birefringence frequency difference $\omega_{bir}$. Thus, sensing a variance in a measurable parameter such as strain or temperature is carried out, for example, by varying the position of the correlation peak along the optical fiber, and, at a desired position, varying the frequency shift $\Omega$ and the frequency difference $\Delta\omega$, and monitoring the magnitude of detected light wave signals as described above.

Figure 9A:
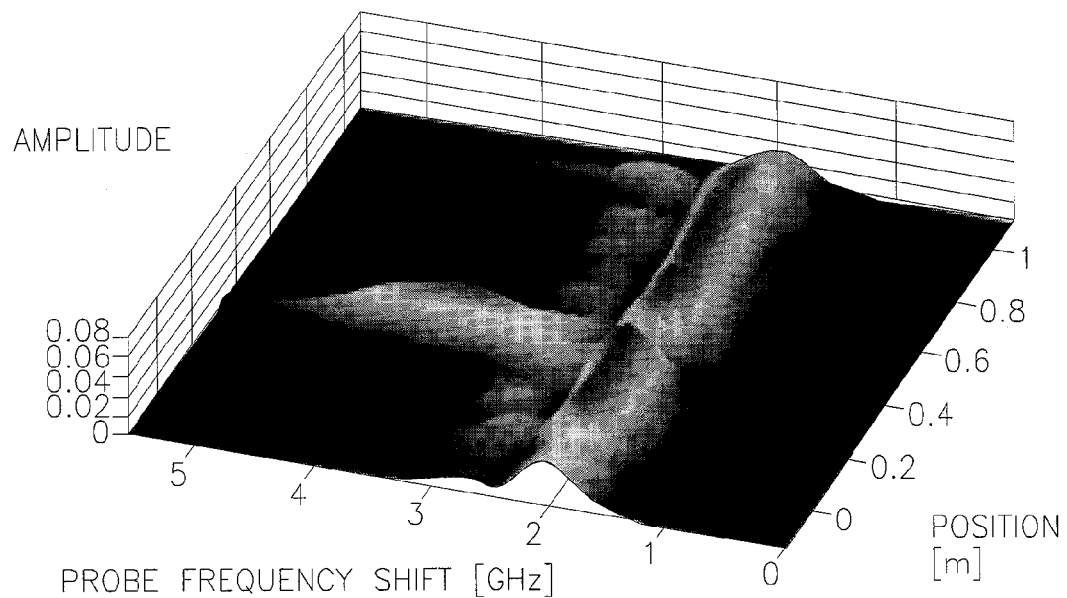
FIGS. 9A and 9B schematically depict exemplary measurement results using the system of FIG. 8, in a form of maps, in accordance with some embodiments of the disclosure.

FIG. 9A is an exemplary measurement result obtained from a system such as schematically illustrated in FIG. 8, employing a 1 meter long PM optical fiber, wherein a portion thereof, 5 cm long, located at about 40 cm from an end of the fiber, is heated using an electric resistor. The measurement result is in a form of a map, depicting the magnitude of detected light wave signals, as a function of position along the PM optical fiber and as a function a frequency difference $\Delta\omega$ between the frequencies of the probe light wave and the corresponding pump light wave. It is noted that a frequency shift $\Omega$ between the frequencies of the first pump light wave and the second pump light wave is tuned to match the Brillouin frequency shift $\Omega_B$ of the heated portion of the optical fiber. High magnitudes of detected signals, compared to the background, are observed around 2.1 GHz along the entire length of the optical fiber, from 0 to 1 m, except at about 0.4 m. At about 0.4 m high magnitude is observed at a frequency of about 4 GHz, thereby demonstrating a 1.9 GHz variance of the birefringence frequency difference $\omega_{bir}$ due to the high temperature in that position.

Figure 9B:
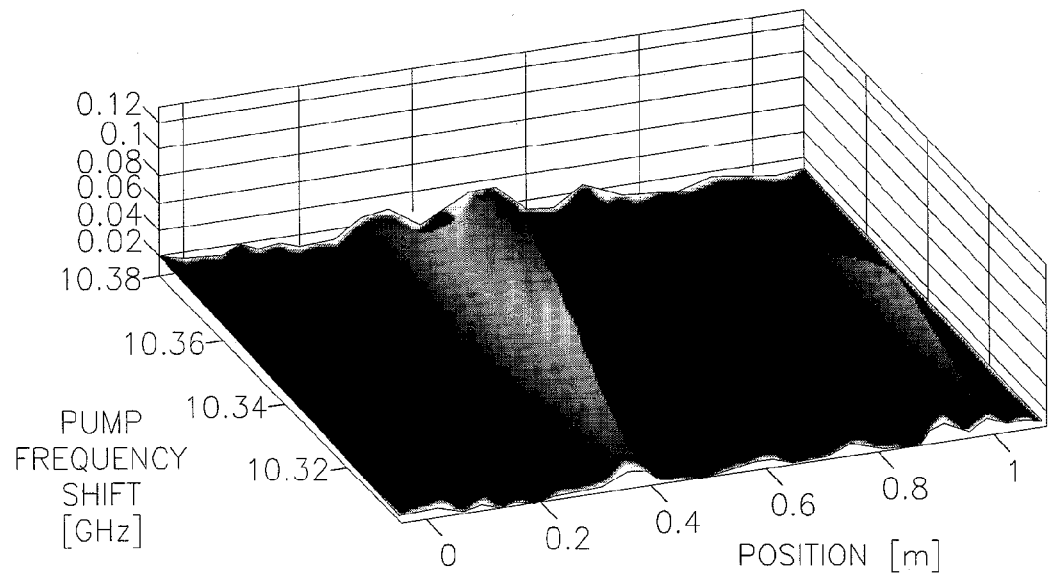

FIG. 9B is another measurement result in a form of a map obtained with the same system as in FIG. 9A. The map depicts the magnitude of detected light wave signals, as a function of position along the PM optical fiber and as a function a frequency shift $\Omega$ between the frequencies of the first pump light wave and the second pump light wave. It is noted that a frequency difference $\Delta\omega$ between the frequencies of the probe light wave and the corresponding pump light wave is tuned to match the birefringence frequency difference $\omega_{bir}$ of the heated portion of the optical fiber. High magnitudes of detected signals, compared to the background, are observed from 10.32 GHz to 10.38 Ghz, at about 0.4 m. High magnitude signals are not observed, however, at any frequency, for portions of the optical fiber outside the heated spot, because, due to the mismatch of the frequency difference $\Delta\omega$ to the birefringence frequency difference $\omega_{bir}$ outside the heated spot, the probe light wave is not reflected effectively from most positions along the optical fiber, regardless of the frequency shift $\Omega$ being selected.

FIG. 9A and FIG. 9B can be seen in color in Primerov, Y. Antman, J. Sancho, A. Zadok, and L. Thevenaz, "Brillouin Distributed Sensing Using Localized and Stationary Dynamic Gratings," paper 8439-7, SPIE Photonics Europe 2012, Brussels, Belgium. Proc. SPIE 8439, 8439-7, 2012, incorporated herein by reference in its entirety.

It is noted that both maps demonstrate high spatial resolution, obtained using the methods described herein, the resolution being better than 5 cm.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. A method for distributed sensing of one or more measurable parameters of an optical fiber, comprising:
generating a first pump light wave having a frequency centered at $\omega_0$;
modulating the first pump light wave to obtain a first modulated pump light wave;
transmitting the first modulated pump light wave into the optical fiber through a first end thereof;
receiving at an end of the optical fiber a scattered light wave signal with a frequency approximately equal to $\omega_0+\Omega_B+\omega_{bir}$ or $\omega_0+\Omega_B-\omega_{bir}$ or $\omega_0-\Omega_B+\omega_{bir}$ or $\omega_0-\Omega_B-\omega_{bir}$, wherein $\Omega_B$ is a Brillouin frequency shift of the optical fiber, and $\omega_{bir}$ is a birefringence frequency difference in the optical fiber;
monitoring at least the frequency of the received light wave signal; and
calculating from the monitored frequency of the received light wave signal a magnitude of a sensed measurable parameter of the optical fiber,
wherein said modulating step comprises modulating at a rate higher than about 1 GHz and lower than about 100 GHz using an anharmonic modulation signal, and wherein the modulation is frequency modulation or phase modulation, thereby enhancing a spatial resolution of said sensing.

2. The method of claim 1, wherein the measurable parameters are selected from the group consisting of strain and temperature.

3. The method of claim 1, wherein the optical fiber is deployed so as to interface, mechanically or thermally, a monitored object, at one or more locations along the length of the optical fiber.

4. The method of claim 1, wherein the monitored light wave signals are generated within the optical fiber by stimulated Brillouin scattering of the first pump light wave transmitted into the optical fiber.

5. The method of claim 1 wherein the first pump light wave comprises at least one pulse of light, and said modulating step comprises modulating the light frequency to vary within a range $$\left(\omega_0 - \frac{\Delta\omega}{2}, \omega_0 + \frac{\Delta\omega}{2}\right)$$

during the at least one pulse period, and wherein $$\frac{\Delta\omega}{2\pi}$$

is greater than about 1 GHz and lower than about 100 GHz.

6. The method of claim 5, wherein the light frequency is varied linearly between $$\omega_0 - \frac{\Delta\omega}{2} \text{ and } \omega_0 + \frac{\Delta\omega}{2}$$

during the at least one pulse period.

7. The method of claim 5 wherein said monitoring step includes measuring a time of arrival of the received light wave signal.

8. The method of claim 5 wherein said receiving step comprises filtering the received light wave signal in a matched filter, thereby obtaining a pulse corresponding to the received light wave signals and having a pulse width shorter than the pulse width of the at least one pulse of the pump light wave.

9. The method of claim 1 further comprising:
generating a generic random signal having a frequency centered substantially between 1 GHz and 100 GHz; and
generating a first random signal by delaying the generic random signal by a time delay $\Delta T_1 \geq 0$;
wherein said modulating the first pump light wave step comprises modulating the phase of the first pump light wave by the first random signal.

10. The method of claim 9 further comprising:
generating a probe light wave having a frequency centered at $\omega_1$, wherein $\omega_1$ is controllably tunable and shifted from $\omega_0$ by approximately $\Omega_B$, $\Omega_B$ being a Brillouin frequency shift of the optical fiber; and
transmitting the probe light wave into the optical fiber through a second end thereof.

11. The method of claim 10 further comprising:
generating a second random signal by delaying the generic random signal by a time delay $\Delta T_2 \geq 0$, and
modulating the phase of the probe light wave by the second random signal.

12. The method of claim 9, wherein the generic random signal is a binary pseudo-random bit sequence signal comprising sequences of length M and bit duration T, assuming bit values of "0" and "1" with equal probabilities, wherein in said step of modulating the phase of the first pump light wave by the first random signal, a varies the phase by $C$ radians, and a "1" varies the phase by $(C+\pi)$ radians, C being substantially constant.

13. The method of claim 12 wherein the bit time duration T is varied to affect a scan of a sensed location along the optical fiber and a distance of a sensed location from an end of the optical fiber is calculated using a value of T.

14. The method of claim 11 wherein at least one of the time delays $\Delta T_1$ and $\Delta T_2$ is varied to affect a scan of a sensed location along the optical fiber and a distance of a sensed location from an end of the optical fiber is calculated using values of $\Delta T_1$ and $\Delta T_2$.

15. The method of claim 1 wherein the optical fiber is a polarization maintaining optical fiber and the method further comprises, prior to said step of transmitting the first pump light wave, polarizing the first pump light wave along a pre-selected first polarization direction $\vec{r}$, substantially equal to a direction of a principal axis $\vec{x}$ of the polarization maintaining optical fiber.

16. The method of claim 15, further comprising:
generating a generic random signal having a frequency centered substantially between 1 GHz and 100 GHz; and
generating a first random signal by delaying the generic random signal by a time delay $\Delta T \geq 0$, wherein said modulating the first pump light wave step comprises modulating the phase of the first pump light wave by the first random signal;
generating a second pump light wave having a frequency of $\omega_1$, wherein $\omega_1$ is controllably tunable and shifted from $\omega_0$ by approximately $\Omega_B$, $\Omega_B$ being a Brillouin frequency shift of the optical fiber;
generating a second random signal by delaying the generic random signal by a time delay $\Delta T_2 \geq 0$;
modulating the phase of the second pump light wave by the second pseudo-random signal;
polarizing the second pump light wave along the pre-selected first polarization direction of the first pump light wave $\vec{r}$; and
transmitting the second pump light wave into the optical fiber through a second end thereof.

17. The method of claim 16 further comprising:
generating a probe light wave having a frequency of $\omega_2$, wherein $\omega_2$ is controllably tunable and shifted from $\omega_0$ by approximately $\omega_{bir}$, $\omega_{bir}$ being a birefringence frequency difference in the optical fiber;
polarizing the probe light wave along a second polarization direction substantially equal to a direction of a second principal axis $\vec{\gamma}$ of the optical fiber; and
transmitting the probe light wave into the optical fiber through the first end thereof,
wherein said step of receiving at an end of the optical fiber a scattered light wave signal, comprises receiving at the first end of the optical fiber a scattered light wave signal, having a frequency approximately equal to $\omega_{sig}$, and
wherein is $\omega_{sig}$ shifted from the frequency $\omega_2$ of the probe signal by approximately $\Omega_B$, $\Omega_B$ being a Brillouin frequency shift of the optical fiber.

18. The method of claim 10, further comprising modulating at least one of the first pump light wave, the second pump light wave and the probe light wave by pulse modulation.

19. The method of claim 18, further comprising synchronizing the pulse modulation of at least one of the first pump light wave, the second pump light wave and the probe light wave with at least one phase modulation modulating the first pump light wave, the second pump light wave and the probe light wave.

20. A device for distributed sensing of one or more measurable parameters of an optical fiber, comprising a phase modulator for modulating a pump light wave in accordance with the method of claim 9.

21. A device for distributed sensing of an optical fiber, configured for transmitting a modulated pump light wave into the optical fiber through an end thereof, and for receiving a scattered light wave signal from an end thereof, and comprising:
- a light source configured for generating a coherent light wave having a frequency of $\omega_0$;
- functionally associated with said light source, a modulator configured for modulating the phase or the frequency of the coherent light wave, thereby generating a modulated pump light wave; and
- functionally associated with said modulator, a modulation signal generator configured for generating an anharmonic modulation signal to modulate the phase or the frequency of the coherent light source by said modulator,
- wherein the modulation signal generated by said modulation signal generator varies the frequency of the coherent light wave by a frequency greater than 1 GHz and smaller than 100 GHz.

22. The device of claim 21, wherein said modulator is a frequency modulator and the device further comprises a pulse modulator functionally associated with said light source generator for generating at least one pulse of the pump light wave,
- wherein said frequency modulator modulates the frequency of the pump light wave to vary substantially linearly within a range $$\left(\omega_0 - \frac{\Delta\omega}{2}, \omega_0 + \frac{\Delta\omega}{2}\right)$$

during the at least one pulse period, and wherein $$\frac{\Delta\omega}{2\pi}$$

is greater than about 1 GHz and lower than about 100 GHz.

23. The device of claim 21, wherein said modulator is a phase modulator and the modulation signal generated by said modulation signal generator, is a random signal.

24. The device of claim 21, wherein the modulation signal generated by said modulation signal generator is a pseudo-random bit sequence signal.

25. The device of claim 21, wherein said optical fiber is a polarization maintaining optical fiber.

* * * * *